(12) United States Patent
Lawler

(10) Patent No.: US 7,223,731 B2
(45) Date of Patent: May 29, 2007

(54) THROMBOSPONDIN-1 TYPE 1 REPEAT POLYPEPTIDES

(75) Inventor: John W. Lawler, Swampscott, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 520 days.

(21) Appl. No.: 10/296,733

(22) PCT Filed: May 25, 2001

(86) PCT No.: PCT/US01/17250

§ 371 (c)(1),
(2), (4) Date: Jul. 2, 2003

(87) PCT Pub. No.: WO01/91781

PCT Pub. Date: Dec. 6, 2001

(65) Prior Publication Data

US 2004/0110131 A1 Jun. 10, 2004

Related U.S. Application Data

(60) Provisional application No. 60/207,994, filed on May 26, 2000.

(51) Int. Cl.
*A61K 38/00* (2006.01)

(52) U.S. Cl. .................. 514/12; 530/350; 530/300; 530/324

(58) Field of Classification Search ............... None
See application file for complete search history.

(56) References Cited

U.S. PATENT DOCUMENTS

| | | | |
|---|---|---|---|
| 5,190,918 A | 3/1993 | Deutch et al. |
| 5,190,920 A | 3/1993 | Eyal et al. |
| 5,200,397 A | 4/1993 | Deutch et al. |
| 5,426,100 A | 6/1995 | Deutch et al. |
| 5,648,461 A | 7/1997 | Eval et al. |
| 5,770,563 A | 6/1998 | Roberts et al. |
| 6,051,549 A | 4/2000 | Roberts et al. |

FOREIGN PATENT DOCUMENTS

| WO | WO 00/44908 | 8/2000 |
|---|---|---|
| WO | WO 01/23561 A2 | 4/2001 |

OTHER PUBLICATIONS

Skolnick et al. (Trends in Biotech., 18(1):34-39, 2000).*
Lawler et al J. Cell Biol. vol. 103 p. 1635 (1986).*
Johnson et al, Cancer Treatment Reviews vol. 2 p. 1-31 (1975).*
Dawson, D.W., et al., "Three Distinct d-Amino Acid Substitutions Confer Potent Antiangiogenic Activity on an Inactive Peptide Derived from a Thrombospondin-1 Type Repeat," *Molecular Pharmacology*, 55:332-338 (1999).
Guo, N., et al., "Antiproliferative and Antitumor Activities of D-Reverse Peptides Derived from the Second Type-1 Repeat of Thrombospondin-1," *Journal of Peptide Research*, 50:210-221 (1997).
Guo, N., et al., "Thrombospondin 1 and Type 1 Repeat Polypeptides 1 Specifically Induce Apoptosis of Endothelial Cells," *Cancer Research*, 57:1735-1742 (1997).
Iruela-Arispe, M.L., et al., "Inhibition of Angiogensis by Thrombospondin-1 Is Mediated by 2 Independent Regions Within the Type 1 Repeats," *Circulation*, 100:1423-1431 (1999).
Kyriakides, T.R., et al., Mice that Lack the Angiogenesis Inhibitor, Thrombospondin 2, Mount an Altered Foreign Body Reaction Characterized by Increased Vascularity, *Proc. Natl. Acad. Sci.*, 96:4449-4454 (1999).
Miao, W., et al., "Thrombospondin-1 Type 1 Repeat Recombinant Proteins Inhibit Tumor Growth Through Transforming Growth Factor-β-Dependent and—Independent Mechanisms," *Cancer Research*, 61: 7830-7839 (2001).
Scalise, T., et al., "Interaction of Recombinant Procollagen and Properdin Modules of Thrombospondin-1 with Heparin and Bibrinogen/Fibrin," *Journal of Biological Chemistry*, 274:430-437 (1999).
Tolsma, S.S., et al., "Peptides Derived from Two Separate Domains of the Matrix Protein Thrombospondin-1 Have Anti-Angiogenic Activity," *Journal of Cell Biology*, 122:497-511 (1993).
Volpert, O.V., et al., "A Human Fibrosarcoma Inhibits Systemic Angiogenesis and the Growth of Experimental Metastases Via Thrombospondin-1," Proc. Natl. Acad. Sci.
Guo, N., et al., "Differential Roles of Protein Kinase C and Pertussis Toxin-Sensitive G-binding Proteins in Modulation of Melanoma Cell Proliferation and Motility by Thrombospondin 1," *Cancer Research*, 58:3154-3162 (1998).
Schultz-Cherry, S., et al., "Regulation of Transforming Growth Factor-β Activation by Discrete Sequences of Thrombospondin 1," *Journal of Biological Chemistry*, 270:7304-7310 (1995).

* cited by examiner

*Primary Examiner*—Sheela J. Huff
(74) *Attorney, Agent, or Firm*—Hamilton, Brook, Smith & Reynolds, P.C.

(57) ABSTRACT

Thrombospondin-1 (TSP-1) is a potent inhibitor of tumor growth and angiogenesis. To elucidate the molecular mechanisms that are involved in the inhibition of tumor growth by the type 1 repeats (TSRs), recombinant versions of these motifs have been produced and have been assayed for their ability to inhibit the growth of experimental B16F10 and Lewis lung carcinomas. Recombinant proteins that contain all three TSRs (3TSR) or the second TSR with (TSR2+RFK) or without (TSR2) the transforming growth factor beta (TGFβ) activating sequence (RFK) have been expressed in *Drosophila* S2 cells. A recombinant protein containing all three type 1 repeats of TSP-2 and a recombinant protein containing the second TSR with the RFK sequence altered to QFK have also been produced. The data indicate that the TSRs inhibit tumor growth by inhibition of angiogenesis and regulation of tumor cell growth and apoptosis. The regulation of tumor cell growth and apoptosis is RFK-dependent while the inhibition of angiogenesis is not. The invention relates to polypeptides based on the amino acid sequence of human TSP-1 type 1 repeats. The polypeptides, variants, fragments and mutants thereof can be made by recombinant methods or can be made by chemical synthesis. The polypeptides can be formulated into pharmaceutical compositions and used in methods of therapy to reduce tumor growth.

16 Claims, 11 Drawing Sheets human thrombospondin-1

```
NH2
     1 NRIPESGGDNSVFDIFELTGAARKGSGRRLVKGPDPSSPAFRIEDANLIPPVPDDKFQDL
    61 VDAVRTEKGFLLLASLRQMKKTRGTLLALERKDHSGQVFSVVSNGKAGTLDLSLTVQGKQ
   121 HVVSVEEALLATGQWKSITLFVQEDRAQLYIDCRKMENAELDVPIQSVFTRDLASIARLR
   181 IAKGGVNDNFQGVLQNVRFVFGTTPEDILRNKGCSSSTSVLLTLDNNVⓃGSSPAIRTNY

241 IGHKTKDLQAICGISCDELSSM

P
   263 VLELRGLRTIVTTLQDSIRKVTRENKELANELRRPPLCYHNGVQYRNNE
   312 EWTVDSCTECHCQNSVTICKKVSCPIMPCSⓃATVPDGECCPRCWPSDSA type 1
   361 DDGWSPWSEWTSCSTSCGNGIQQRGRSCDSLNNR----CEGSSVQTRTCHIQECDKRFKQ
   417 DGGWSHWSPWSSCSVTCGDGVITRIRLCNSPSPQMNGKPCEGEARETKACKKDACPI
   474 NGGWGPWSPWDICSVTCGGGVQKRSRLCNⓃPTPQFGGKDCVGDVTENQICNKQDCPI type 2
   531 DGCLSNP--CFAGV---KCT---SYPDGSWKCGACPPGYSG--------NGIQCTDV
   572 DECKEVPDACFNHNGEHRCEN----TDPGYNCLPCPPRFTGSQPFGQGVEHATANKQVCKPR
   630 NPCTDGTHDCNKNA---KCNYLGHYSDPMYRC-ECKFPGYAG--------NGIICGE

674 DTDLDGWPNENLVCVAⓃATYHCKK

698 DNCPNLPNSGQEDYDKDGIGDACDD--DDDNDKIPDDR
   734 DNCPFHYNPAQYDYDRDDVGDRC
   757 DNCPYNHNPDQADTDNNGEGDACAA--DIDGDGILNER
   793 DNCQYVYNVDQRDTDMDGVGDQC
   816 DNCPLEHNPDQLDSDSDRKIGDTCDNNQDIDEDGHQNNL
   854 DNCPYVPNANQADHDKDGKGDACDH--DDDNDGIPDDK
   890 DNCRLVPNFDQKDQKDSDGDGRGDACKD--DFDHDSVPDID type 3
COOH
   926 DICPENVDISETDFRRFQMIPLDPKGTSQNDPNWVRHQGKELVQTVNCDPGLAVGYDEF
   986 NAVDFSGTFFINTERDDDYAGFVFGYQSSSRFYVVMNKQVTQSYWDTⓃPTRAQGYSGLSV
  1046 KVVⓃSTTGPGEHLRNALWHTGNTPGQVRTLWHDPRHIGWKDFTAYRWRLSHRPKTGFIRV
  1106 VMYEGKKIMADSGPIYDKTYAGGRLGLFVFSQEMVFFSDLKYECRDP
```

FIG. 7

```
   1 mlwalallal gigprasagd hvkdtsfdlf sisninrkti gakqfrgpdp gvpayrfvrf
  61 dyippvntdd lnrivklarr kegffltaql kqdrksrgtl lvlegpgtsq rqfeivsngp
 121 gdtldlnywv egnqhtnfle dvgladsqwk nvtvqvasdt yslyvgcdli dsvtleepfy
 181 eqlevdrsrm yvakgasres hfrgllqnvh lvfadsvedi lskkscqhsq gaevntiseh
 241 tetlhlsphi ttdlvvqgve kaqevcthsc eelsnmmnel sglhvmvnql sknlervssd
 301 nqflleligg plktrnmsac vqegrifaen etwvvdsctt ctckkfktvc hqitcspatc
 361 anpsfvegec cpscshsads degwspwaew tecsvtcgsg tqqrgrscdv tsntclgpsi
 421 qtrtcslgkc dtrirqnggw shwspwsscs vtcgvgnvtr irlcnspvpq mggknckgsg
 481 retkpcqrdp cpidgrwspw spwsactvtc aggirersrv cnspepqygg kdcvgdvteh
 541 qmcnkrscpi dgclsnpcfp gakcnsfpdg swscgscpvg flgngthced ldecavvtdi
 601 cfstnkaprc vntnpgfhcl cppprykgnq pfgvgledar tekqvcepen pckdkthsch
 661 knaeciylgh fsdpmykcec qigyagdgli cgedsdldgw pnnnlvcatn atyhcikdnc
 721 pklpnsgqed fdkdgigdac dedddndgvs dekdncqllf nprqldydkd evgdrcdncp
 781 yvhnpaqidt dnngegdacs vdidgddvfn erdncpyvyn tdqrdtdgdg vgdhcdncpl
 841 mhnpdqidqd ndlvgdqcdn nedidddghq nnqdncpyis nsnqadhdnd gkgdacdsdd
 901 dndgvpddrd ncrlvfnpdq edsdgdgrgd ickddfdndn vpdiddvcpe nnaitetdfr
 961 nfqmvpldpk gttqidpnwv irhqgkelvq tansdpgiav gfdefgsvdf sgtfyvntdr
1021 dddyagfvfg yqsssrfyvv mwkqvtqtyw edkpsraygy sgvslkvvns ttgtgehlrn
1081 alwhtgnteg qvrtlwhdpk nigwkdytay rwhlihrpkt gymrvlvheg kqvmadsgpi
1141 ydqtyaggrl glfvfsqemv yfsdlkyecr da
```

FIG. 10

```
   1 mvwrlvllal wvwpstqagh qdkdttfdlf sisninrkti gakqfrgpdp gvpayrfvrf
  61 dyippvnadd lskitkimrq kegffltaql kqdgksrgtl lalegpglsq rqfeivsngp
 121 adtldltywi dgtrhvvsle dvgladsqwk nvtvqvaget yslhvgcdli gpvaldepfy
 181 ehlqaeksrm yvakgsares hfrgllqnvh lvfensvedi lskkgcqqgq gaeinaisen
 241 tetlrlgphv tteyvgpsse rrpevcersc eelgnmvqel sglhvlvnql senlkrvsnd
 301 nqflweligg ppktrnmsac wqdgrffaen etwvvdsctt ctckkfktic hqitcppatc
 361 aspsfvegec cpsclhsvdg eegwspwaew tqcsvtcgsg tqqrgrscdv tsntclgpsi
 421 qtracslskc dtrirqdggw shwspwsscs vtcgvgnitr irlcnspvpq mggknckgsg
 481 retkacqgap cpidgrwspw spwsactvtc aggirertrv cnspepqygg kacvgdvqer
 541 qmcnkrscpv dgclsnpcfp gaqcssfpdg swscgfcpvg flgngthced ldecalvpdi
 601 cfstskvprc vntqpgfhcl pcppryrgnq pvgvgleaak tekqvcepen pckdkthnch
 661 khaeciylgh fsdpmykcec qtgyagdgli cgedsdldgw pnlnlvcatn atyhcikdnc
 721 phlpnsgqed fdkdgigdac dddddndgvt dekdncqllf nprqadydkd evgdrcdncp
 781 yvhnpaqidt dnngegdacs vdidgddvfn erdncpyvyn tdqrdtdgdg vgdhcdncpl
 841 vhnpdqtdvd ndlvgdqcdn nedidddghq mnqdncpyis nanqadhdrd gqgdacdpdd
 901 dndgvpddrd ncrlvfnpdq edlgdgrgd ickddfdndn ipdiddvcpe nnaisetdfr
 961 nfqmvpldpk gttqidpnwv irhqgkelvq tansdpgiav gfdefgsvdf sgtfyvntdr
1021 dddyagfvfg yqsssrfyvv mwkqvtqtyw edqptraygy sgvslkvvns ttgtgehlrn
1081 alwhtgntpg qvrtlwhdpr nigwkdytay rwhlthrpkt gyirvlvheg kqvmadsgpi
1141 ydqtyaggrl glfvfsqemv yfsdlkyecr di
```

THROMBOSPONDIN-1 TYPE 1 REPEAT POLYPEPTIDES

RELATED APPLICATIONS

This application claims the benefit of U.S. Provisional Application No. 60/207,994 filed May 26, 2000, the entire teachings of which are incorporated herein by reference.

GOVERNMENT SUPPORT

The invention was supported, in whole or in part, by a grant HL28749 from the National Heart, Lung and Blood Institute of the National Institutes of Health. The Government has certain rights in the invention.

BACKGROUND OF THE INVENTION

Thrombospondin-1 is a potent inhibitor of angiogenesis (for a review, see Dawson, D. W. and Bouck, N. P., "Thrombospondin as an inhibitor of angiogenesis," In: B. A. Teicher (eds.), *Antiangiogenic Agents in Cancer Therapy*, pp. 185–203, Totowa, N.J.; Humana Press, Inc., 1999). It inhibits endothelial cell growth, migration and tube formation in vitro (Panetti, T. S., et al., *J. Lab. Clin. Med.*, 129: 208–216, 1997). In vitro assays have shown that platelet thrombospondin-1 is involved in thrombosis, fibrinolysis, wound healing, inflammation, tumor cell metastasis and angiogenesis. The major form of thrombospondin secreted by platelets and endothelial cells is TSP-1. Thrombospondin-1 (TSP-1) is an angiogenesis inhibitor. Thrombospondin-1 has three copies of the TSR. TSP-1 is a trimeric molecule. Thus, the fully assembled protein contains nine TSRs.

The ingrowth of new capillary networks into developing tumors is essential for the progression of cancer. As pointed out in a review by Folkman (Folkman, J., *Proc. Natl. Acad. Sci. USA* 95: 9064–9066, 1998), antiangiogenic therapy has little toxicity, does not require the therapeutic agent to enter tumor cells or cross the blood-brain barrier, controls tumor growth independently of growth of tumor cell heterogeneity, and does not induce drug resistance. Thus, the development of pharmaceuticals that inhibit the process of angiogenesis or can inhibit abnormal cell proliferation by other mechanisms is an important therapeutic goal.

SUMMARY OF THE INVENTION

The invention involves the use of a recombinant or synthetic version or a segment of the type 1 repeat domain (TSR) of human thrombospondin-1 (TSP-1) or variants, fragments or mutants thereof to inhibit tumor growth by angiogenic or other activity. In particular, good anti-tumor activity is obtained if the protein or protein fragment employed includes the KRFK sequence (SEQ ID NO: 28) from the C-terminal end of the first TSR and a sufficient portion of the N-terminal end of the second TSR (through the first disulfide bond) to give the protein or protein fragment tertiary structure similar to the wild-type TSRs. A cDNA encoding amino acids 411 through 473 of human TSP-1 (SEQ ID NO: 22) has been cloned into the pMT/BiP/V5His A expression vector. The recombinant protein has been expressed and purified by standard protocols. This protein is a potent inhibitor of tumor growth in mice. The growth of B16F10 melanoma cells and Lewis lung carcinoma cells is inhibited by 86% and 77%, respectively, with a single daily interperitonial dose of 2.5 mg/kg/day. The inclusion of the sequence KRFK (SEQ ID NO: 28) at the N-terminus of the recombinant protein significantly increased the anti-tumor activity of this protein. The protein that contains the KRFK sequence (SEQ ID NO: 28) is termed broadly herein a polypeptide comprising the second type 1 repeat of human TSP-1, but not comprising the RFK sequence, or the other domains of TSP-1; also, a "TSR2+RFK polypeptide or protein." At 1 mg/kg/day the TSR2+RFK protein described in the Examples inhibited B16F10 tumor growth by 80%. The protein that lacks the KRFK sequence is termed broadly herein a polypeptide comprising the second type 1 repeat of human TSP-1, and the RFK sequence, but not the other domains of TSP-1; also, a "TSR2 polypeptide or protein" The TSR2 protein described in the Examples inhibited tumor growth by 38%. This result is contrary to previously published results using synthetic peptides and an orthotopic model of breast cancer, in that the KRFK sequence (SEQ ID NO: 28) was previously reported to lack anti-tumor activity.

The mechanism of action for the inhibition of tumor growth by a TSR2+RFK protein involves inhibition of angiogenesis, induction of tumor cell apoptosis and inhibition of tumor cell proliferation. The latter two activities appear to require the KRFK sequence (SEQ ID NO: 28) in that these effects are not observed with the TSR2 protein. The KRFK sequence (SEQ ID NO: 28) of TSP-1 has not been reported to induce tumor cell apoptosis previously.

The invention relates to polypeptides based on the amino acid sequence of human thrombospondin 1, and more specifically relates to: (1) a polypeptide comprising the three type 1 repeats of human TSP-1, but not comprising the other domains of TSP-1 (a 3TSR or 3TSR (TSP1) polypeptide or protein); (2) a polypeptide comprising the second type 1 repeat of human TSP-1, but not comprising the RFK sequence or the other domains of TSP-1 (a TSR2 polypeptide or protein); (3) a polypeptide comprising the second type 1 repeat of human TSP-1 and the RFK sequence, but not the other domains of TSP-1 (a TSR2+RFK polypeptide or protein); (4) a polypeptide comprising the second type 1 repeat of human TSP-1 and the RFK sequence altered to QFK, but not the other domains of TSP-1 (a TSR2+QFK polypeptide or protein), and (5) a polypeptide comprising all three type 1 repeats of human TSP-2, but not the other domains of TSP-2 [a 3TSR (TSP2) polypeptide or protein]. See, for the domains of TSP-1, Table 1.

Further embodiments are fragments, variants and mutants of these polypeptides having amino acid sequences that differ from the type 1 repeat segment of the human TSP-1 or human TSP-2. Variants can have, for example, flanking amino acid sequence, amino acid substitutions, deletions, or additions, or some combination. The polypeptides, variants, fragments and mutants can be made by recombinant methods or can be made by chemical synthesis, using L-amino acids, analogues or derivatives thereof, or D-amino acids or related compounds, or they can be made of only L-amino acids.

Also described herein are nucleic acid molecules involved in the making of constructs encoding the polypeptides described herein, vectors, and host cells that can be used in recombinant methods of producing the polypeptides.

The polypeptides can be formulated into pharmaceutical compositions and used in methods of therapy to reduce tumor growth. For example, a TSR2+RFK polypeptide, or a conservative variant thereof, can be combined with a pharmaceutically acceptable carrier. A fragment of the TSR2+RFK with up to 30 consecutive amino acid residues deleted relative to the TSR2+RFK polypeptide having SEQ ID NO: 22 can also be formulated into a pharmaceutical composition. Further, variants of the TSR2+RFK polypeptide, especially conservative variants, and variants at least 70%, 80%, 90% or 95% identical in amino acid sequence to TSR2+RFK can be formulated with a pharmaceutically acceptable carrier.

The TSR2+RFK polypeptides, fragments, variants and mutants thereof, as well as other polypeptides described herein, can be administered to a human patient in an amount sufficient to induce apoptosis, inhibit neovascularization, or otherwise inhibit growth in cancerous cells (e.g., cells within a tumor).

A further embodiment of the invention is a method of killing cancerous cells in a patient, comprising administering to said patient an amount of a TSR2+RFK polypeptide fragment sufficient to induce apoptosis in said cancerous cells, wherein said fragment has at least about the same apoptotic and anti-angiogenic activity as TSR2+RFK as illustrated in the Examples, and has up to 30 consecutive amino acids deleted from the carboxy terminus of TSR2+RFK. In variations of the method, a variant which is at least 70%, 80%, 90% or 95% identical in amino acid sequence to TSR2+RFK is administered to a patient, wherein the variant can be combined with a pharmaceutically acceptable carrier.

BRIEF DESCRIPTION OF THE DRAWINGS

FIG. 7 is a representation of the amino acid sequence of human TSP-1 (SEQ ID NO: 1). The type 1 repeats of TSP-1 are, as illustrated here, 1) amino acids 361–416; 2) amino acids 417–473; and 3) amino acids 474–530. Also shown in FIG. 7 are the complete type 2 repeats, the type 3 repeats, and the procollagen homology region.

FIG. 10 is a representation of the amino acid sequence of mouse thrombospondin 2, including signal sequence (SEQ ID NO: 24). See National Center for Biotechnology Information Accession No. NP 035711, PID g6755779, as in Laherty, C. D. et al., *J. Biol. Chem.* 267(5):3274–3281, 1992.

FIG. 11 is a representation of the amino acid sequence of human thrombospondin 2, including signal sequence (SEQ ID NO: 26). See National Center for Biotechnology Information Accession No. TSHUP2, PID g1070641, as in LaBell, T. L. et al., *Genomics* 12(3):421–429, 1992.

DETAILED DESCRIPTION OF THE INVENTION

Figure 1:
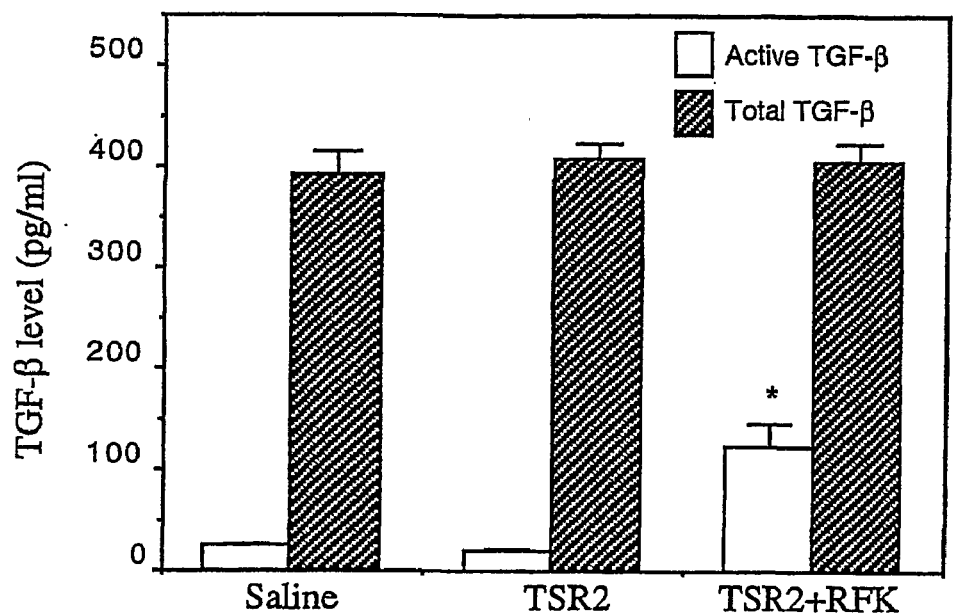
FIG. 1 is a bar graph showing TGFβ activation by the TSR2+RFK protein of the Examples. Saline, the TSR2 or the TSR2+RFK recombinant proteins (5.0 μg/ml) were incubated with B16F10 cells overnight in serum-free DMEM. The levels of active and total TGFβ were determined using the MLEC assay (Abe, M., et al., *Anal. Biochem,* 216:276–84, 1994). The asterisk indicates p<0.005 relative to control.

A description of preferred embodiments of the invention follows.

The data presented here show that administration of recombinant proteins (also herein: "polypeptides") that contain the TSRs of TSP-1 or the TSRs of TSP-2 inhibit the growth of experimental tumors. Inhibition has been observed with both B16F10 melanoma and Lewis lung carcinoma cell lines. The 3TSR and TSR2+RFK proteins are relatively potent, showing 70%–80% inhibition of tumor volume at 2.5 mg/kg/day. This concentration is 100–300 nmoles/kg/day. Injection with intact TSP-1 protein at 0.25 mg/kg/day (0.6 nmoles/kg/day) resulted in a 56% reduction of tumor growth, indicating that the intact protein is considerably more active than the recombinant proteins at low doses.

Several activities of the TSRs may contribute to the inhibition of tumor growth. These include the ability to (1) inhibit angiogenesis, (2) reduce tumor cell proliferation, (3) activate TGFβ, and (4) regulate extracellular proteases. The results described here show that systemic treatment with the TSRs of TSP-1 or TSP-2 reduces vessel density in tumors.

The rate of tumor cell apoptosis is a key factor in the determination of the rate of tumor growth (Parangi, P., et al., *Proc. Natl. Acad. Sci.* (*USA*), 93: 2002–2007, 1996; Naik, P. N., et al., *Genes & Dev.,* 10:2105–2116, 1996). Described herein are results showing that TSP-1 proteins that include the RFK sequence significantly increase the rate of tumor cell apoptosis. Whereas TSP-1 has been reported to inhibit tumor cell proliferation and induce endothelial cell apoptosis, this study demonstrates that the TSR-containing proteins induce tumor cell apoptosis (Guo, NH., et al., *Cancer Res.,* 57:1735–1742, 1997; Guo, N.-H., et al., *Cancer Res.,* 58: 3154–3162, 1998). This activity is enhanced by the addition of the DKRFK (SEQ ID NO: 2) sequence at the $NH_2$-terminus, because the TSR2 protein did not increase the level of apoptosis of the tumor cells to the same extent as the TSR2+RFK protein. An increase in tumor cell apoptosis is frequently associated with anti-angiogenic therapy due to the decrease in nutrients that is associated with the decrease in blood supply. These data herein indicate that increased tumor cell apoptosis occurs as a direct result of the TSR2+RFK protein treatment rather than indirectly through inhibition of angiogenesis. Whereas, the TSR2+RFK and TSR2 proteins reduce vessel density to comparable levels, the TSR2+RFK protein has a more profound effect on tumor cell apoptosis. In addition, this protein significantly decreases tumor cell proliferation in vivo.

The data presented here indicate that inclusion of the additional sequence DKRFK (SEQ ID NO: 2) at the N-terminus of the TSR2 protein to yield the TSR2+RFK protein significantly increases the anti-tumor activity of the protein. The difference in activity of the protein that contains the DKRFK (SEQ ID NO: 2) sequence as compared to the one that does not may be due to the activation of TGFβ, an increased affinity for heparan sulfate proteoglycans or an unidentified activity of this sequence. The additional sequence in the TSR2+RFK protein includes the RFK sequence that reportedly activates TGFβ (Schultz-Cherry, S., et al., *J. Biol. Chem.,* 270: 7304–7310, 1995). In experiments using the culture supernatant from B16F10 cells, it was shown that the TSR2+RFK protein activates TGFβ, while the TSR2 protein does not. TGFβ has pleiotropic effects on tumor growth. At early stages of tumorigenesis, TGFβ may act as a tumor suppressor gene (Engle, S. J., et al., *Cancer Research,* 59: 3379–3386, 1999; Tang, B., et al., *Nature Med.,* 4: 802–807, 1998). TGFβ can induce apoptosis of several different tumor cell lines (Guo, Y. and Kypianou, N., *Cancer Research,* 59: 1366–1371, 1999 and references therein). At later stages of tumor growth, TGFβ can stimulate angiogenesis through the recruitment of inflammatory and stromal cells (Pepper, M., *Cytokine & Growth Factor Reviews,* 8: 21–43, 1997).

The data presented here indicate that recombinant proteins that include the TSRs have therapeutic value as inhibitors of tumor growth. They act to inhibit angiogenesis and to induce tumor cell apoptosis. Since these mechanisms of action are probably different from other inhibitors of neoplasia, a combinational approach that includes TSRs with other inhibitors of tumor growth can be an effective treatment for cancer.

Figure 8:
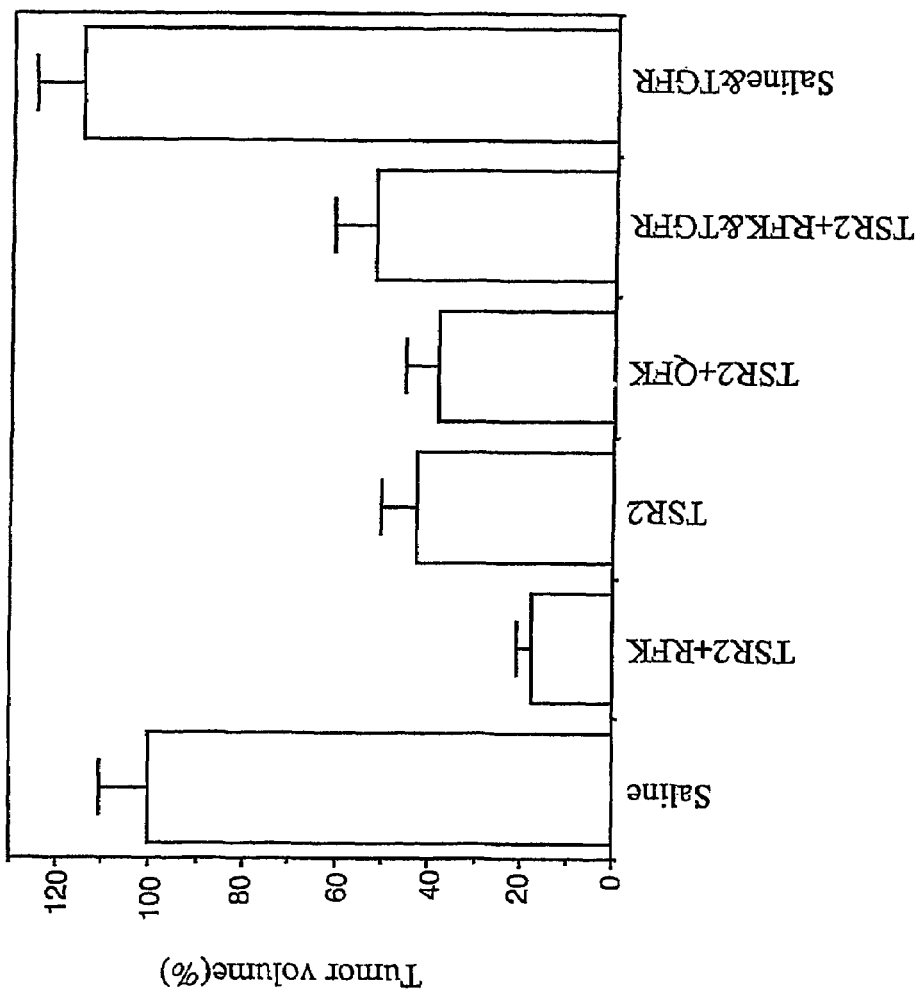
FIG. 8 is a bar graph showing the effect of treatment with recombinant, TSP-1 peptides or controls on the tumor volume from melanoma B16F10 in C57BL/6 mice.
Figure 9:
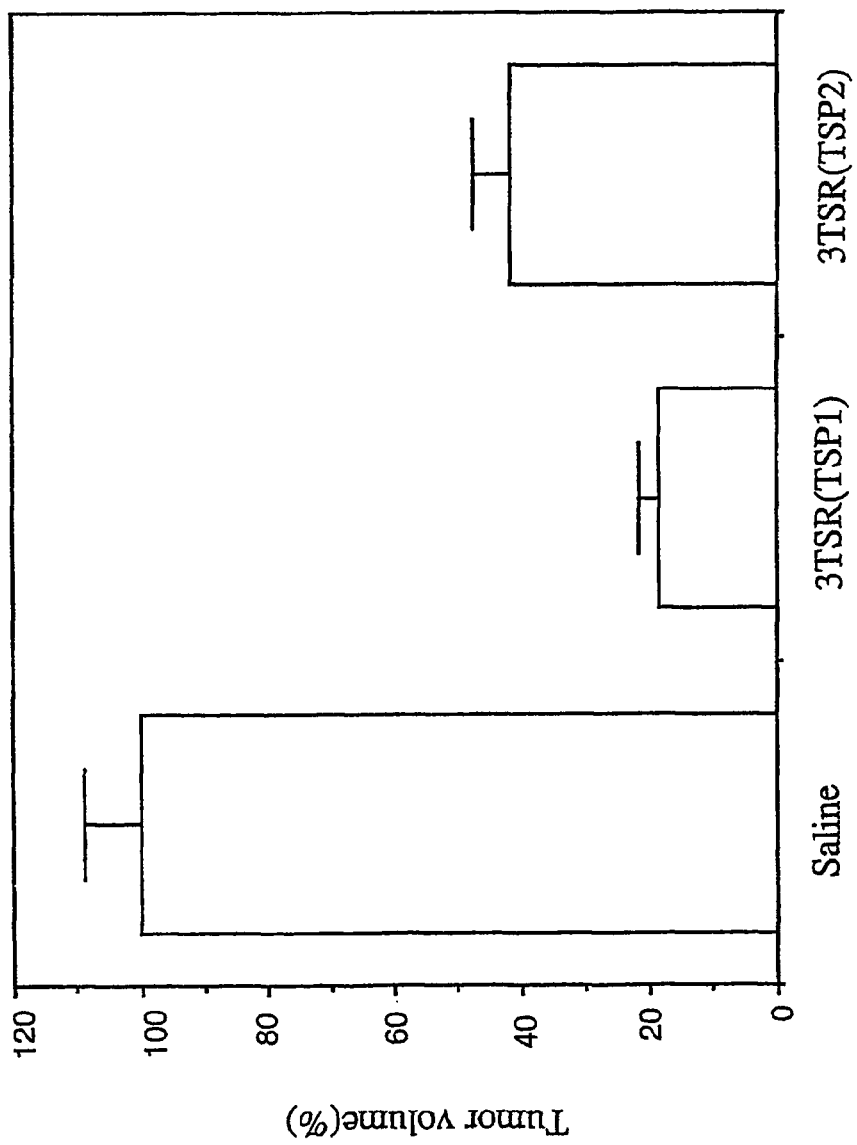
FIG. 9 is a bar graph showing the effect of treatment with recombinant TSP peptides or saline as control on the tumor volume from melanoma B16F10 in C57Bl/6 mice.

The RFK sequence mediates the ability of TSP-1 to activate TGFβ (Schultz-Cherry, S. et al., *J. Biol. Chem.* 270:7304–7310, 1995). Mutation of the arginine residue (R) to glutamine (Q) abolishes the ability of synthetic peptides to activate TGFβ. A recombinant version of the TSR2+RFK protein was produced in which Q is substituted for R. This protein is designated TSR2+QFK. In the B16F10 experimental tumor model, TSR2+QFK is less effective as an inhibitor of tumor growth than TSR2+RFK (FIG. 8). The activity of TSR2+QFK is comparable to that of TSR2. A recombinant version of all three type 1 repeats of mouse TSP-2 has also been prepared. TSP2 has the sequence RIR in the position where TSP-1 has RFK, and has been reported to be unable to activate TFGβ (Schultz-Cherry, S. et al, *J. Biol. Chem.* 270:7304–7310, 1995). The recombinant protein that includes all three TSRs of mouse TSP-2 is significantly less potent as an inhibitor of B16F10 tumor growth than all three type 1 repeats of human TSP-1 (FIG. 9).

The ability of TSR2+RFK to inhibit tumor growth was also evaluated in the presence of a soluble form of the TGFβ receptor. Systemic injection of this reagent has been shown to inhibit endogenous TGFβ activity (Smith, J. D. et al., *Circ. Res.* 84:1212–22, 1999). Concurrent treatment of B16F10 tumor-bearing mice with TSR2+RFK and the soluble form of the TGFβ receptor resulted in a significant loss of anti-tumor activity (FIG. 8). The level of inhibition of tumor growth under these circumstances was comparable to that observed with the TSR2 or TSR2+QFK proteins. Animals that received control injections of saline with the soluble TGFβ receptor produced tumors that are about 15% larger than those produced in the mice that received only saline. This suggests that TGFβ that is activated by endogenous TSP-1 or by other means is normally suppressing tumor growth.

Taken together, these data indicate that the ability of the TSR2+RFK protein to inhibit tumor growth is due in part to the activation of TGFβ by the RFK sequence. This conclusion is consistent with the observation that both TSR2+RFK and TGFβ inhibit B16F10 tumor cell proliferation in vitro.

The recombinant protein is more effective than the intact TSP-1 protein in inhibiting tumor growth. The recombinant protein includes specific active sequences and does not include other domains of TSP-2 or TSP-1 that may decrease the over all activity. See Table 1 for active sequences of TSP-1 (taken from chapter 2, "The Primary Structure of the Thrombospondins" In *The Thrombospondin Gene Family* (J. C. Adams et al., eds.) Springer-Verlag, Heidelberg (1995. The recombinant protein can be made in large quantities and does not require human tissue as a source of protein. This protein is folded like the wild-type protein and can be more stable in circulation than peptides. It can also be modified to include sequences that will target it to tumor tissue. Because these proteins are derived from portions of human proteins, they should not be immunogenic in humans.

TABLE 1

Active Regions of Interest Within Thrombospondin-1

| Domain | Sequence | Function |
| --- | --- | --- |
| Procollagen homology | NGVQYRN (SEQ ID NO: 4) | Anti-angiogenesis |
| Type 1 repeats | CSVTCG (SEQ ID NO: 5) | Cell binding |
|  | WSXWSXW (SEQ ID NO: 6) GGWSHW (SEQ ID NO: 7) | Heparin binding TGF-β and Fibronectin binding |
|  | RFK SPWDICSVTCGGGVQKRSR (SEQ ID NO: 8) | TGF-β activation Anti-angiogenesis |
| Type 2 repeats | DVDEC$(X)_6$C$(X)_8$CENTDPGYNCLPC (SEQ ID NO: 9) | Calcium binding |

In one aspect, the invention comprises polynucleotides or nucleic acid molecules that encode polypeptides whose amino acid sequences are derived from human TSP-1. By the genomic structure, the type 1 repeats of TSP-1 are amino acid residues 359–414 (first), amino acid residues 415–473 (second), and 474–531 (third). In another case, the polypeptides encoded by the polynucleotides of the invention are fragments or variants of the immediately aforementioned polypeptides, which have activity that is similar in quality and quantity (for example, plus or minus one order of magnitude in an assay) to the anti-angiogenic and/or apoptosis increasing and/or anti-tumor growth activity of the polypeptides tested in the Examples. A fragment of a TSR2+ RFK, TSR2+QFK, or TSR2 polypeptide can, for instance, have up to 30 (any number from 1 to 30) consecutive amino acid residues deleted from the carboxy terminus, relative to SEQ ID NO: 22, SEQ ID NO: 23, and SEQ ID NO: 21, respectively. The carboxy terminal deletion in a fragment of a polypeptide can be, for example, 5, 10, 15, 20 or 25 consecutive amino acids.

The polynucleotides that encode the polypeptides described herein can be made by recombinant methods, can be made synthetically, can be replicated by enzymes in in vitro (e.g., PCR) or in vivo systems (e.g., by suitable host cells, when inserted into a vector appropriate for replication within the host cells), or can be made by a combination of methods. The polynucleotides of the invention can include DNA and its RNA counterpart.

As used herein, "nucleic acid," "nucleic acid molecule," "oligonucleotide" and "polynucleotide" include DNA and RNA and chemical derivatives thereof, including phosphorothioate derivatives and RNA and DNA molecules having a radioactive isotope or a chemical adduct such as a fluorophore, chromophore or biotin (which can be referred to as a "label"). The RNA counterpart of a DNA is a polymer of ribonucleotide units, wherein the nucleotide sequence can be depicted as having the base U (uracil) at sites within a molecule where DNA has the base T (thymidine).

Isolated nucleic acid molecules or polynucleotides can be purified from a natural source or can be made recombinantly. Polynucleotides referred to herein as "isolated" are polynucleotides purified to a state beyond that in which they exist in cells. They include polynucleotides obtained by methods described herein, similar methods or other suitable methods, and also include essentially pure polynucleotides produced by chemical synthesis or by combinations of biological and chemical methods, and recombinant polynucleotides that have been isolated. The term "isolated" as used herein for nucleic acid molecules, indicates that the molecule in question exists in a physical milieu distinct from that in which it occurs in nature. For example, an isolated polynucleotide may be substantially isolated with respect to the complex cellular milieu in which it naturally occurs, and may even be purified essentially to homogeneity, for example as determined by agarose or polyacrylamide gel electrophoresis or by $A_{260}/A_{280}$ measurements, but may also have further cofactors or molecular stabilizers (for instance, buffers or salts) added.

The invention further relates to fusion proteins comprising, for example: (1) a polypeptide comprising the three type 1 repeats of human TSP-1, but not comprising the other domains of TSP-1; (2) a polypeptide comprising the second type 1 repeat of human TSP-1, but not comprising the RFK sequence or the other domains of TSP-1; (3) a polypeptide comprising the second type 1 repeat of human TSP-1 and the RFK sequence, but not the other domains of TSP-1; (4) a polypeptide comprising the second type 1 repeat of human TSP-1 and the RFK sequence altered to QFK, but not the other domains of TSP-1; or (5) a polypeptide comprising all three type 1 repeats of human TSP-2, but not the other domains of TSP-2, wherein any one of (1), (2), (3), (4) or (5) is linked to a second moiety not occurring in TSP-1 or TSP-2 as found in nature. The second moiety can be an amino acid, peptide or polypeptide, and can have enzymatic or binding activity of its own. The first moiety can be in an N-terminal location, C-terminal location or internal to the fusion protein. The second moiety can comprise a linker sequence and an affinity ligand, for example.

Variants of the polypeptide include those having amino acid sequences different from sequences which can be seen as contiguous portions of the sequence in FIG. 7 (which illustrates, for example, amino acid residues 361–530 (SEQ ID NO: 20), 411–473 (SEQ ID NO: 22) and 416–473 (SEQ ID NO: 21)). Variants can have, for instance, several, such as 5 to 10, 1 to 5, or 4, 3, 2 or 1 amino acids substituted, deleted, or added, in any combination, compared to the sequences which are a portion of the sequence in FIG. 7. In one embodiment, variants have silent substitutions, additions and/or deletions that do not significantly alter the properties and activities of the polypeptide. See Table 2 for examples of conservative amino acid substitutions. Variants can also be modified polypeptides in which one or more amino acid residues are modified.

The invention also encompasses variant polypeptides having a lower degree of identity but having sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr and Trp. Guidance concerning which amino acid changes are likely to be phenotypically silent is found in Bowie et al., *Science* 247:1306–1310 (1990). See also Table 2.

TABLE 2

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

"Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two polypeptides is occupied by serine, then they are identical at that position. The identity between two sequences is a direct function of the number of matching or identical positions, e.g., if half (e.g., 5 positions in a polymer 10 subunits in length) of the positions in two peptide or compound sequences are identical, then the two sequences are 50% identical; if 90% of the positions, e.g., 9 of 10 are matched, the two sequences share 90% sequence identity. By way of example, the amino acid sequences $R_2R_5R_7R_{10}R_6R_3$ and $R_9R_8R_1R_{10}R_6R_3$ have 3 of 6 positions in common, and therefore share 50% sequence identity, while the sequences $R_2R_5R_7R_{10}R_6R_3$ and $R_8R_1R_{10}R_6R_3$ have 3 of 5 positions in common, and therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_2R_5R_7R_{10}R_6R_3$ and $R_2R_5R_7R_{10}R_3$ have 5 out of 6 positions in common, and therefore share 83.3% sequence identity.

Identity is often measured using sequence analysis software e.g., BLASTN or BLASTP (available at website for National Center for Biotechnology Information, National Institutes of Health). The default parameters for comparing two sequences (e.g., "Blast"-ing two sequences against each other by BLASTN (for nucleotide sequences) are reward for match=1, penalty for mismatch=-2, open gap=5, extension gap=2. When using BLASTP for protein sequences, the default parameters are reward for match=0, penalty for mismatch=0, open gap=11, and extension gap=1.

When two sequences share "sequence homology," it is meant that the two sequences differ from each other only by conservative substitutions. For polypeptide sequences, such conservative substitutions consist of substitution of one amino acid residue at a given position in the sequence for another amino acid residue of the same class (e.g., amino acids that share characteristics of hydrophobicity, charge, pK or other conformational or chemical properties, e.g., valine for leucine, arginine for lysine), or by one or more non-conservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one non-polar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another; or the use of a chemically derivatized residue in place of a non-derivatized residue; provided that the polypeptide displays the requisite biological activity. Two sequences which share sequence homology may called "sequence homologs."

Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Embodiments of the invention include not only the polypeptides consisting of SEQ ID NOs 20, 21, 22, 23, 25 and 27, but also any polypeptide which is at least 70% or 80%, more preferably 90%, and still more preferably, 95% identical to any of the TSP polypeptides identified herein by SEQ ID NO, wherein the polypeptide has at least about the same anti-angiogenic or apoptotic or anti-tumor activity as the polypeptide identified by SEQ ID NO. These activities can be determined by methods described herein, for example, the TUNEL assay for apoptosis (Abe, M. et al., *Anal. Biochem.* 216:276–84, 1994), the measurement of capillary density for anti-angiogenic effect, as described in Example 2, or the counting of tumor cells to determine cell proliferation or the inhibition thereof. Other methods known in the art can also be used.

A further embodiment of the invention is a 3TSR, TSR2, TSR2+RFK or TSR2+QFK polypeptide, or an active variant or fragment of any of the foregoing, wherein the region of the polypeptide derived from the human TSP-1 amino acid sequence is flanked on one or both ends by other amino acid residues having an amino acid sequence which is not found as the human TSP-1 amino acid sequence that naturally occurs adjacent to the region. Flanking peptide regions can be, for example, 1, 2, 3, 4 or 5, 5–10, 10–20, or 20–30 amino acid residues in length.

Further embodiments of the invention are mutants of the 3TSR, TSR2, TSR2+RFK, TSR2+QFK, or 3TSR (TSP2) polypeptides. By "mutant" is meant a polypeptide that includes any change in the amino acid sequence relative to the amino acid sequence of the polypeptide described herein by SEQ ID NO. Such changes can arise either spontaneously or by manipulations by man, by chemical energy (e.g., X-ray), or by other forms of chemical mutagenesis, or by genetic engineering, or as a result of mating or other forms of exchange of genetic information. Mutations include, e.g., base substitutions, deletions, insertions, inversions, translocations, or duplications. Mutant forms of the polypeptides can display either increased or decreased anti-angiogenic activity and either increased or decreased tumor growth inhibition activity relative to the polypeptides identified herein by SEQ ID NO. Such mutants may or may not also comprise additional amino acids derived from the process of cloning, e.g., amino acid residues or amino acid sequences corresponding to full or partial linker sequences.

Mutants/fragments of the anti-angiogenic and/or anti-tumor polypeptides of the present invention can be generated by PCR cloning. To make such fragments, PCR primers can be designed from known nucleic acid sequences in such a way that each set of primers will amplify a predicted region of the coding sequence for the starting polypeptide. These amplified DNAs are then cloned into an appropriate expression vector, such as the pET22b vector, and the expressed polypeptide can ben tested for its anti-angiogenic activity and anti-tumor activity. Alternatively, mutants and fragments can be produced by chemical synthesis methods.

Proteins and polypeptides described herein can be assessed for their angiogenic activity by using an assay such as the one described in Tolsma, S. S. et al., *J. Cell Biol.* 122(2):497–511 (1993), an assay which measures the migration of bovine adrenal capillary endothelial cells in culture, or an assay which tests migration of cells into a sponge containing an agent to be tested for activity. A further test for angiogenesis, which can also be adapted also to test anti-angiogenesis activity, is described in Polverini, P. J. et al., *Methods. Enzymol.* 198:440–450 (1991). More recently, methods to quantitate inhibition of tumor vascularization, and to quantitate inhibition of corneal neovascularization, were described in Blezinger, P. et al., *Nature Biotechnology* 17:343–348, 1999.

Another aspect of the invention relates to a method of producing a polypeptide of the invention, or a variant or fragment thereof, and to expression systems and host cells containing a vector appropriate for expression of a polypeptide of the invention. Cells that express such a polypeptide or a variant or a fragment thereof can be made and maintained in culture, under conditions suitable for expression, to produce protein for isolation. These cells can be procaryotic or eucaryotic. Examples of prokaryotic cells that can be used for expression (as "host cells"; "cell" including herein cells of tissues, cell cultures, cell strains and cell lines) include *Escherichia coli, Bacillus subtilis* and other bacteria. Examples of eucaryotic cells that can be used for expression include yeasts such as *Saccharomyces cerevisiae, Schizosaccharomyces pombe, Pichia pastoris* and other lower eukaryotic cells, and cells of higher eukaryotes such as those from insects and mammals. Suitable cells of mammalian origin include primary cells, and cell lines such as CHO, HeLa, 3T3, BHK, COS, 293, and Jurkat cells. Suitable cells of insect origin include primary cells, and cell lines such as SF9 and High five cells. (See, e.g., Ausubel, F. M. et al., eds. *Current Protocols in Molecular Biology*, Greene Publishing Associates and John Wiley & Sons Inc., (containing Supplements up through 2001)).

In one embodiment, host cells that produce a recombinant polypeptide, variant, or a fragment thereof can be made as follows. A gene encoding a polypeptide variant or fragment described herein can be inserted into a nucleic acid vector, e.g., a DNA vector, such as a plasmid, virus or other suitable replicon (including vectors suitable for use in gene therapy, such as those derived from adenovirus or others; see, for example Xu, M. et al., *Molecular Genetics and Metabolism* 63:103–109, 1998) present in the cell as a single copy or multiple copies, or the gene can be integrated in a host cell chromosome. A suitable replicon or integrated gene can contain all or part of the coding sequence for the polypeptide, fragment or variant, operably linked to one or more expression control regions whereby the coding sequence is under the control of transcription signals and linked to appropriate translation signals to permit translation. The vector can be introduced into cells by a method appropriate to the type of host cells (e.g., transformation, electroporation, infection). For expression from the gene, the host cells can be maintained under appropriate conditions (e.g., in the presence of inducer, normal growth conditions, etc.). Proteins or polypeptides thus produced can be recovered (e.g., from the cells, the periplasmic space, culture medium) using suitable techniques.

The invention also relates to isolated proteins or polypeptides. Isolated polypeptides or fragments or variants can be purified from a natural source or can be made recombinantly. Proteins or polypeptides referred to herein as "isolated" are proteins or polypeptides purified to a state beyond that in which they exist in cells and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. Thus, the term "isolated" as used herein, indicates that the polypeptide in question exists in a physical milieu distinct from the cell in which its biosynthesis occurs. For example, an isolated polypeptide of the invention can be purified essentially to homogeneity, for example as determined by PAGE or column chromatography (for example, HPLC), but may also have further cofactors or molecular stabilizers added to the purified protein to enhance activity. In one embodiment, proteins or polypeptides are isolated to a state at least about 75% pure; more preferably at least about 85% pure, and still more preferably at least about 95% pure, as determined by Coomassie blue staining of proteins on SDS-polyacrylamide gels.

"Polypeptide" as used herein indicates a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations and the like. In addition, the polypeptides, fragments and variants of the invention can be synthesized, by laboratory or by biosynthetic methods, using amino acids that carry modifications such as glycosylation, acetylation, phosphorylation, or chemical adducts for the purpose of providing a chromophoric, fluorophoric, radioactive, or biotin label, for example.

Fusion proteins comprising a polypeptide described herein can be produced by a variety of methods. For example, a polypeptide can be produced by the insertion of a TSP gene or portion thereof into a suitable expression vector, such as Bluescript SK +/− (Stratagene), pGEX-4T-2 (Pharmacia), pET-15b, pET-20b(+) or pET-24(+) (Novagen). The resulting construct can be introduced into a suitable host cell for expression. Upon expression, the polypeptide can be purified from a cell lysate by means of a suitable affinity matrix (see e.g., *Current Protocols in Molecular Biology* (Ausubel, F. M. et al., eds., Vol. 2, pp. 16.4.1–16.7.8, containing supplements up through 2001).

Polypeptides of the invention can be recovered and purified from cell cultures by well-known methods. The recombinant polypeptide can be purified by ammonium sulfate precipitation, heparin-Sepharose affinity chromatography, gel filtration chromatography and/or sucrose gradient ultracentrifugation using standard techniques. Further methods that can be used for purification of the polypeptide include ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

Also included in the inventions are compositions containing, as a biological ingredient, a polypeptide of the invention, or a variant, fragment or mutant thereof to inhibit angiogenesis and/or increase apoptosis or inhibit tumor growth by other mechanisms in mammalian tissues, and use of such compositions in the treatment of diseases and conditions characterized by, or associated with, angiogenic activity or misregulated growth. Such methods can involve administration by oral, topical, injection, implantation, sustained release, or other delivery methods that bring one or more of the polypeptides in contact with cells whose growth is to be inhibited.

The present invention includes a method of treating an angiogenesis-mediated disease or cancer with a therapeutically effective amount of one or more polypeptides having anti-angiogenic activity or anti-tumor activity as described herein. Angiogenesis-mediated diseases can include, but are not limited to, cancers, solid tumors, tumor metastasis, benign tumors (e.g., hemangiomas, acoustic neuromas, neurofibromas, trachomas, and pyogenic granulomas), rheumatoid arthritis, psoriasis, ocular angiogenic diseases (e.g., diabetic retinopathy, retinopathy of prematurity, macular degeneration, corneal graft rejection, neovascular glaucoma, retrolental fibroplasia, rubeosis), Osler-Webber Syndrome, myocardial angiogenesis, plaque neovascularization, telangiectasia, hemophiliac joints, angiofibroma, and wound granulation. Polypeptide antiangiogenic agents and/or anti-tumor agents can be used, for example, after surgery or radiation to prevent recurrence of metastases, in combination with conventional chemotherapy, immunotherapy, or various types of gene therapy not necessarily directed against angiogenesis.

"Cancer" means neoplastic growth, hyperplastic or proliferative growth or a pathological state of abnormal cellular development, and includes solid tumors, non-solid tumors, and any abnormal cellular proliferation, such as that seen in leukemia. As used herein, "cancer" also means angiogenesis-dependent cancers and tumors, i.e., tumors that require for their growth (expansion in volume and/or mass) an increase in the number and density of the blood vessels supplying them with blood. "Regression" refers to the reduction of tumor mass and size. As used herein, the term "therapeutically effective amount" means the total amount of each active component of the composition or method that is sufficient to show a meaningful benefit to a treated human or other mammal, i.e., treatment, healing, prevention or amelioration of the relevant medical condition, or an increase in rate of treatment, healing, prevention or amelioration of such conditions. More specifically, for example, a therapeutically effective amount of an anti-angiogenic polypeptide can cause a measurable reduction in the size or numbers of tumors, or in their rate of growth or multiplication, compared to untreated tumors. Other methods of assessing a "therapeutically effective amount," can include the result that blood vessel formation is measurably reduced in treated tissues compared to untreated tissues.

One or more anti-tumor polypeptides as described herein may be used in combination with other compositions and procedures for the treatment of diseases. For example, a tumor may be treated conventionally with surgery, radiation, chemotherapy, or immunotherapy, combined with anti-angiogenic polypeptides, and then anti-tumor polypeptides may be subsequently administered to the patient to extend the dormancy of micrometastases and to stabilize and inhibit the growth of any residual primary tumor.

The compositions may further contain other agents which either enhance the activity of the protein or complement its activity or use in treatment, such as chemotherapeutic or radioactive agents. Such additional factors and/or agents may be included in the composition to produce a synergistic effect with protein of the invention, or to minimize side effects. Additionally, the compositions of the present invention may be administered concurrently with other therapies, e.g., in conjunction with a chemotherapy, immunotherapy or radiation therapy regimen.

The anti-tumor composition of the present invention may be a solid, liquid or aerosol and may be administered by any known route of administration. Examples of solid compositions include pills, creams, and implantable dosage units. The pills may be administered orally, the therapeutic creams may be administered topically. The implantable dosage unit may be administered locally, for example at a tumor site, or may be implanted for systemic release of the composition, for example subcutaneously. Examples of liquid compositions include formulations adapted for injection subcutaneously, intravenously, intraarterially, and formulations for topical and intraocular administration. Examples of aerosol formulation include inhaler formulation for administration to the lungs.

One or more polypeptides described herein can be provided as isolated and substantially purified polypeptides in pharmaceutically acceptable formulations (including aqueous or nonaqueous carriers or solvents) using formulation methods known to those of ordinary skill in the art. These formulations can be administered by standard routes. In general, the combinations can be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the polypeptides can be incorporated into biodegradable polymers allowing for sustained release of the compound, the polymers being implanted in the vicinity of where drug delivery is desired, for example, at the site of a tumor, or implanted so that the polypeptides are slowly released systemically. Osmotic minipumps may also be used to provide controlled delivery of high concentrations of polypeptide through cannulae to the site of interest, such as directly into a growth or into the vascular supply to that growth. The biodegradable polymers and their use are described, for example, in detail in Brem et al. (1991, *J. Neurosurg.* 74:441–446), which is hereby incorporated by reference in its entirety.

As used herein, the terms "pharmaceutically acceptable," as it refers to compositions, carriers, diluents and reagents, represents that the materials are capable of administration to or upon a mammal with a minimum of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as injectables either as liquid solutions or suspensions, however, solid forms suitable for solution, or suspensions, in liquid prior to use can also be prepared. The preparation can also be emulsified, for example, in liposomes.

The dosage of the polypeptide of the present invention will depend on the disease state or condition being treated and other clinical factors such as weight and condition of the human or animal and the route of administration of the compound. It is to be understood that the present invention has application for both human and veterinary use. The methods of the present invention contemplate single as well as multiple administrations, given either simultaneously or over an extended period of time.

The present invention also encompasses gene therapy whereby a polynucleotide encoding one or more polypeptides or one or more variants or fragments thereof, is introduced and regulated in a patient. Various methods of transferring or delivering DNA to cells for expression of the gene product protein, otherwise referred to as gene therapy, are disclosed in *Gene Transfer into Mammalian Somatic Cells in Vivo*, N. Yang (1992) *Crit. Rev. Biotechnol.* 12(4): 335–356, which is hereby incorporated by reference. Gene therapy encompasses incorporation of DNA sequences into somatic cells or germ line cells for use in either ex vivo or in vivo therapy. Gene therapy can function to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. For example, a gene encoding a polypeptide described herein can be inserted into tumor cells of a patient and thus inhibit angiogenesis.

Gene transfer methods for gene therapy fall into three broad categories: physical (e.g., electroporation, direct gene transfer and particle bombardment), chemical (e.g., lipid-based carriers, or other non-viral vectors) and biological (e.g., virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of anti-angiogenic or anti-tumor polypeptide-encoding DNA and linked regulatory sequences.

Chemical methods of gene therapy may involve a lipid based compound, not necessarily a liposome, to transfer the DNA across the cell membrane. Lipofectins or cytofectins, lipid-based positive ions that bind to negatively charged DNA, make a complex that can cross the cell membrane and allow the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the bloodstream and then target cells that have the receptor will specifically bind the ligand and transport the ligand-DNA complex into the cell.

A plasmid or other type of suitable vector can be constructed to facilitate the expression of one or more gene sequences encoding a TSP-derived polypeptide as described herein. Strong promoter regions and enhancer regions may be used to facilitate the construction of such a plasmid. If the plasmid is not to be introduced directly at the site of the tumor cells to be treated, it maybe also be desirable to construct the plasmid such that a segment of DNA encoding a signal peptide is inserted immediately 5' to the coding region for the polypeptide.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct the tissue-specific expression of foreign genes, cis-acting regulatory elements or promoters that are known to be tissue-specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV40, vaccinia and other DNA viruses. Replication-defective murine retroviral vectors have been widely utilized gene transfer vectors.

Carrier mediated gene transfer in vivo can be used to transfect foreign DNA into cells. The carrier-DNA complex can be conveniently introduced into body fluids or the bloodstream and then site-specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

The gene therapy protocol for transfecting anti-tumor polypeptides into a patient may either be through integration of a gene encoding a polypeptide into the genome of the cells, into minichromosomes or as a separate replicating or non-replicating DNA construct in the cytoplasm or nucleoplasm of the cell. Anti-angiogenic polypeptide expression may continue for a long period of time or the carrier-DNA complex may be reinjected periodically to maintain a desired level of the polypeptide in the cell, the tissue or organ or a determined blood level.

Gene transfer into muscle cells especially has been tested and found to be safe. In a recent test, biologically active endostatin was produced by expression plasmids injected into muscle cells, and inhibited tumor vascularization and the growth of subcutaneous tumors and metastatic lung tumors. (Blezinger, P. et al., *Nature Biotechnology* 17:343–348, 1999). An appropriate dose of plasmid can be injected intramuscularly, for example, once weekly.

Peptide phage display libraries have been used to identify peptides that bind specifically to the vascular endothelial cells of different organs such as lung, skin, pancreas and intestine (Rajotte, D. et al., *J. Clin. Invest.*, 102:430–437, 1998). The individual binding properties of the vasculature of specific organs can be used in targeting the delivery of an agent, such as a polypeptide, to those vascular cells.

Peptides found to bind to the endothelial cells of capillaries supplying blood to individual organs can be produced in fusion with the TSP-derived polypeptides of the invention, to provide a chemical address to target a particular tissue type of organ. For example, the expression vector described above can be engineered to have a coding sequence for a targeting peptide immediately 5' or immediately 3' of the coding sequence for a TSP-derived polypeptide of the invention. Such vectors can be administered to a tumor-bearing mammal, such as a human, at the site of one or more tumors, or at a distant site, to provide a source of fusion polypeptide by expression of the fusion gene on the vector. Alternatively, a recombinant fusion protein of a targeting peptide and a TSP-derived polypeptide can be produced in host cells cultured in a laboratory or production facility, using an expression vector or using host cells otherwise genetically altered to produce the fusion polypeptide.

Not only have peptides been found that bind specifically to the vascular endothelial cells of different organs, but peptides have been found that bind specifically to molecules exposed on the surface of tumor cells and angiogenic tumor vasculature. See, for example, Burg, M. A. et al., *Cancer Research*, 59:2869–2874, 1999, in which phage display of a peptide library was used to select for phages binding to NG2 proteoglycan, which is expressed on the surface of several different types of tumors.

EXAMPLES

Example 1

Production and Characterization of Recombinant Polypeptides

Human TSP-1 and Recombinant Proteins.

Human TSP-1 was purified from the supernatant of thrombin-treated platelets as described previously (Adams, J. C. and Lawler, J, *Mol. Bio. Cell* 5: 423–437, 1994). Recombinant proteins that included sequences from the type 1 repeats were prepared by PCR using the full-length cDNA for human TSP-1 as a template. A DNA segment encoding a recombinant protein containing all three TSRs of TSP-1 (3TSR, amino acids 361–530; SEQ ID NO: 20) was prepared using the forward primer 475htsp1f (GAT GAT CCC GGG GAC GAC TCT GCG GAC GAT GGC; SEQ ID NO: 10) and the reverse primer 476htsp1r (GAT ACC GGT AAT TGG ACA GTC CTG CTT G; SEQ ID NO: 11). A DNA segment encoding a recombinant protein that contains the second TSR (TSR2, amino acids 416–473; SEQ ID NO: 21) was prepared using the forward primer 537htsp1f (GAT GAT CCC GGG CAG GAT GGT GGC TGG AGC; SEQ ID NO: 12) and the reverse primer 515htsp1r (GAT ACC GGT GAT GGG GCA GGC GTC TTT CTT; SEQ ID NO: 13). To evaluate the role of TGFβ activation on the effect of this recombinant protein, a DNA segment encoding a longer version of the second TSR (TSR2+RFK, amino acids 411–473; SEQ ID NO: 22) that includes the RFK sequence was synthesized using the forward primer 514htsp1f (GAT GAT CCC GGG GAC AAG AGA TTT AAA CAG; SEQ ID NO: 14) and the reverse primer 515htsp1r. All three PCR products were cloned between the XmaI and the AgeI sites of the vector pMT/BiP/V5-HisA (Invitrogen, Carlsbad, Calif.). The recombinant proteins included the vector-derived amino acid sequence RSPWG (SEQ ID NO: 15) at the $NH_2$-terminus and TGHHHHHH (SEQ ID NO: 16) at the COOH-terminus. The fidelity of the PCR products was verified by nucleotide sequencing. Each expression vector was cotransfected into *Drosophila* S2 cells with the selection vector pCoHYGRO according to the manufacturer's protocols (Invitrogen). Transfected cells were selected with hygromycin B and the expression of recombinant polypeptides was monitored by western blotting using the polyclonal antibody R3 that was raised against a fusion protein that contained all three TSRs of TSP-1 (Legrand, C. et al., *Blood*, 79:1995–2003, 1992). For large-scale preparation of recombinant protein, S2 cells were grown in serum-free media for five days. The culture supernatant was centrifuged to remove the cells and dialyzed against 20 mM $NaPO_4$ (pH 7.8) and 500 mM NaCl. The dialysate was applied to a column of ProBond resin (Invitrogen). The column was eluted with 20 mM $NaPO_4$ (pH 6.0), 500 mM NaCl, 500 mM imidazole. The protein eluted with 500 mM imidazole was dialyzed against 20 mM $NaPO_4$ (pH 7.0), and 500 mM NaCl and 1% sucrose was added prior to storage.

Cell Culture.

Human dermal microvessel endothelial cells (HDMEC) were isolated by the procedure of Richard et al., *Exp. Cell Res.* 240:1–6 (1998). The cells were cultured in Vitrogen precoated dishes, and maintained in EBM (Clonetics Corp, San Diego, Calif.) containing 20% fetal bovine serum (FBS), 1 mg/ml hydrocortisone acetate, $5 \times 10^{-5}$ M dibutyryl-cAMP, 200 U/ml penicillin, 100 U/ml streptomycin, 250 mg/ml amphotericin and 2–5 ng/ml VEGF. Murine melanoma B16F10 and murine Lewis lung carcinoma cells were obtained from the ATCC, and were maintained in Dulbecco's Modified Eagle Media (DMEM) supplemented with 10% FBS, 50 mg/ml penicillin, 50 U/ml streptomycin, and 2 mM glutamine (supplemented DMEM). Mink lung epithelial cells (MLECs-Clone 32) that have been stably transfected with an 800 bp fragment of the plasminogen activator inhibitor-1 (PAI-1) promoter fused to the firefly luciferase reporter gene were kindly provided by Dr. Daniel Rifkin (Abe, M. et al., *Anal. Biochem.* 216:276–284, 1994). The transfected MLECs were maintained in supplemented DMEM.

Assay for TGFβ Activation.

B16F10 cells ($2.5 \times 10^5$) were plated in a T25 flask and grown overnight in supplemented DMEM. The cells were rinsed once with 1.0 ml of serum-free DMEM and 2.5 ml of serum-free DMEM containing 5.0 mg/ml of the TSR, or TSR+RFK recombinant protein were added. After an overnight incubation, conditioned media was collected and centrifuged at 12,000 rpm for 5 min to remove cellular debris. Undiluted media was used to determine the level of active TGFβ. The level of total TGFβ was determined by incubating the media at 80° C. for 10 min and diluting 1:5 in DMEM. One hundred microliters of conditioned media were added to wells of a 96-well plate containing $3 \times 10^4$ MLECs and the plates were incubated overnight. A standard curve was constructed by incubating 7.8 to 250 pg/ml of purified TGFβ with the MLECs® & D Systems, Inc. Minneapolis, Minn.) in DMEM. The media was removed and the cells were washed 3 times with cold PBS prior to the addition of 100 ml of lysis buffer (PharMingen, San Diego, Calif.). Luciferase activity was measured using the Enhanced Luciferase Assay Kit PharMingen).

In Vitro Migration Assay.

Cells at passage 7–10 were serum-starved and maintained in EBM with 0.1% BSA (control media) for 20 hours before trypsinization to harvest the cells. Cells were washed in EBM twice and resuspended in control media at a concentration of $1 \times 10^6$ cells/ml. Two hundred ml of cells were packed down and kept frozen. They were lysed and serially diluted by CyQuant reagent (Molecular Probe, Eugene, Oreg.) to be used for standard curve construction.

Transwell membrane (24-well polycarbonate membrane, 8 mM pore size from Corning Costar Corporation, Cambridge, Mass.) coated with Vitrogen (30 mg/ml, Invitrogen) on both sides was used for chemotactic migration experiments. Coated transwells were inverted, 100 ml of cell suspension applied to the top of the membrane and covered by the bottom plate carefully so that the cell suspension stayed on top of the membrane. The cells were allowed to adhere to the coated membrane for two hours in an incubator at 37° C. with 5% $CO_2$. After the adhesion incubation, the plates were re-inverted, the bottom wells were filled with 0.4 ml control media and the top wells were filled with 0.1 ml control media containing testing reagents. The plate was returned to the incubator for 3.5 hours for the cells to migrate. At the end of the incubation, the transwells were washed in PBS and the cells on the bottom side of the membrane (unmigrated cells) were wiped away with a cotton swab. The membranes were cut out by scalpel and placed into 96-well plates and frozen at −80° C. overnight. Two hundred ml of CyQuant reagent were added to each well. Fluorescence reading was done 16 hours later with a SpectraFluor plate reader with excitation at 485 nm and emission at 535 μm. The number of cells migrated was then calculated based on the standard curve.

Characterization of Recombinant Proteins

Three recombinant forms of the type 1 repeats of human TSP-1 have been produced in S2 cells. A particular example of a polypeptide comprising the three type 1 repeats of human TSP-1, but not comprising the other domains of TSP-1 designated "3TSR," has been made, and contains amino acids 361–530 of human TSP-1. This protein has a predicted molecular weight of 20,520 Daltons and an apparent molecular weight of 25,000 Daltons on SDS-PAGE, suggesting that carbohydrates are added by post-translational modification. The 3TSR, TSR+RFK and TSR recombinant proteins were electrophoresed on a 4%–15% gradient gel. The gel was cut in half and duplicate lanes were stained with Coomassie blue, or western blotted with a polyclonal antibody to all three TSRs of human TSP-1.

Each TSR contains six cysteine residues. Consistent with the presence of intrachain disulfide bonds in this protein, the 3TSR protein migrates more rapidly in the absence of reducing agent during SDS-PAGE (Panetti, T. S. et al., *J. Biol. Chem.*, 274:430–437, 1999). A second construct, designated TSR2+RFK, contains the second type 1 repeat of human TSP-1 (amino acids 411–473; SEQ ID NO: 22) and includes the DKRFK (SEQ ID NO: 2) sequence in the $NH_2$-terminal region. The RFK sequence has been shown to be necessary and sufficient for activation of TGFβ (Schultz-Cherry, S. et al., *J. Biol. Chem.*, 270:7304–7310, 1995). An equivalent region of TSP-1 (amino acids 416–473; SEQ ID NO: 21) that excludes the DKRFK (SEQ ID NO: 2) sequence, designated TSR2, has also been expressed. The average level of protein expression is comparable for all three proteins (approximately 24 μg of purified protein from 1 ml of conditioned media). All three proteins react with a polyclonal antibody, designated R3, that was raised against a bacterial fusion protein composed of the type 1 repeats fused to β-galactosidase (Legrand, C. et al., *Blood*, 79:1995–2003, 1992). Taken together, the data indicate that the recombinant proteins produced in S2 cells are similar to the type 1 repeats in the native protein.

Figure 2A:
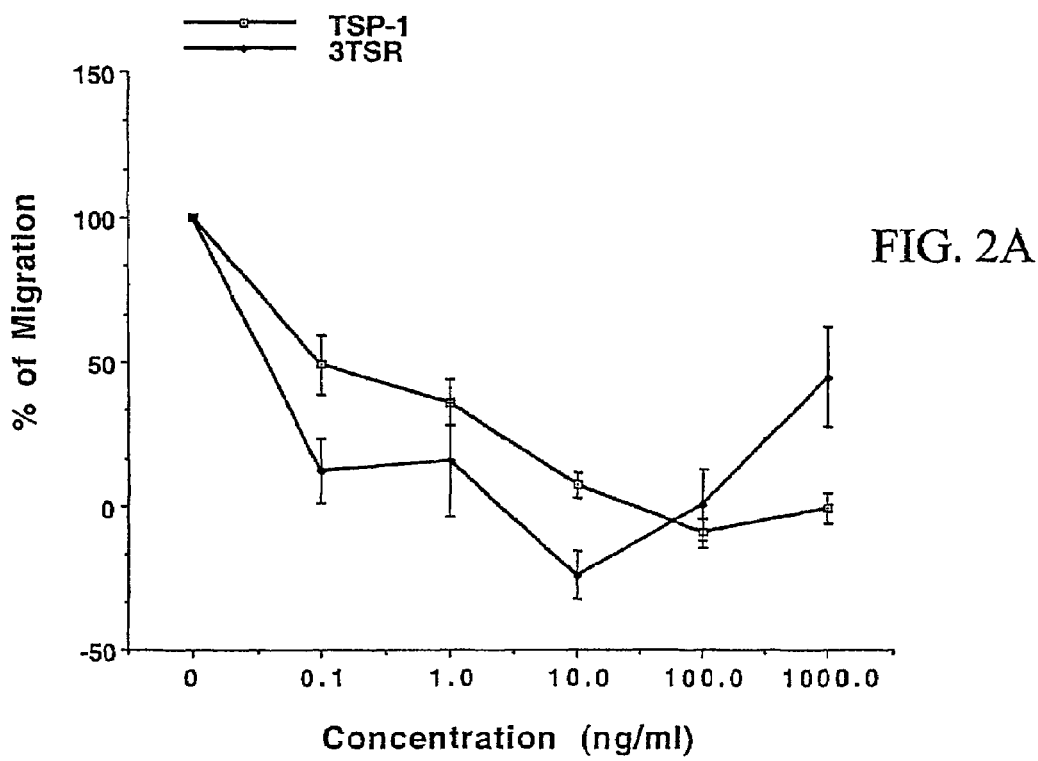
FIGS. 2A and 2B are graphs showing the effect of TSP-1 and the TSR-containing recombinant proteins of the Examples on endothelial cell migration. HDMEC migration in the presence of varying concentrations of TSP-1 (FIG. 2A, open squares), 3TSR (FIG. 2A, filled diamonds), TSR2 (FIG. 2B, open squares) or TSR2+RFK (FIG. 2B, filled diamonds) was determined after four hours. Migration in response to FGF-2 in the absence of inhibitors was considered 100% migration and migration in the absence of FGF-2 was considered 0% migration.
Figure 2B:
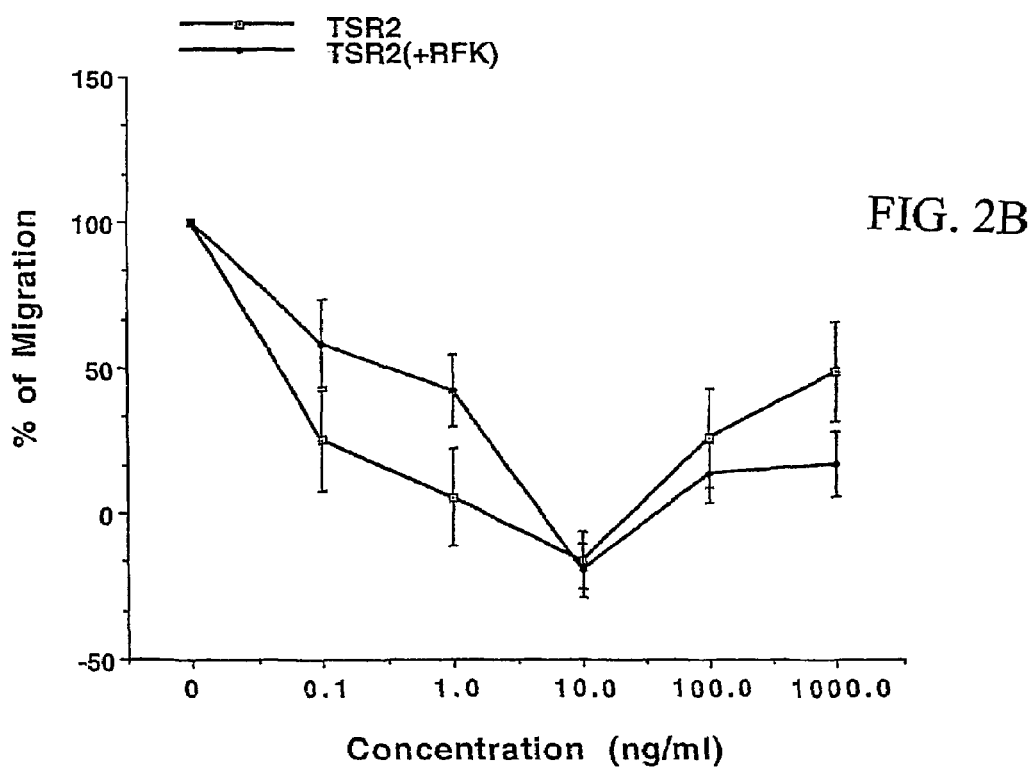

Functionally, the recombinant TSR-containing proteins are similar to the native TSRs in that they activate TGFβ and inhibit endothelial cell migration. In media conditioned by B16F10 melanoma cells, 6.3% of the total TGFβ is in the active form (FIG. 1). Addition of 5 μg/ml of the TSR2+RFK protein to conditioned media increases the level of the active form to 30% of the total TGFβ. By contrast, addition of TSR2 does not result in an increase in the level of active TGFβ in the conditioned media (4.8%). As shown in FIGS. 2A and 2B, TSP-1 is a potent inhibitor of endothelial cell migration in vitro. This inhibition is dose-dependent up to 100 ng/ml of TSP-1, but concentrations of TSP-1 above this level are less effective. This biphasic response has been reported by others (Tolsma, S. S. et al., J. Cell Biol., 122:497–511, 1993). The 3TSR, TSR2 and TSR2+RFK recombinant proteins also inhibit endothelial migration with responses that are similar to TSP-1, on a weight basis. All three recombinant proteins are maximally effective in inhibiting endothelial cell migration at 10 ng/ml (FIGS. 2A and 2B).

Example 2

Testing Effect of Recombinant Polypeptides on Tumor Growth

Primary Tumor Growth Assay.

The proteins for injection were mixed with Polymyxin B-Agarose (Sigma) for 30 minutes at room temperature to remove endotoxin. The endotoxin levels were less than 0.05 EU/mg as determined using the QCL-1000 assay kit (Biowhittaker, Walkersville, Md.). Proteins were filter-sterilized and the protein concentration was determined prior to injection.

Five to eight week old C57BL/6 mice (Taconic, Germantown, N.Y.) were acclimated, caged in groups of four or less and their backs were shaved. Cultured B16F10 melanoma or Lewis lung carcinoma cells ($1 \times 10^6$) were inoculated subcutaneously on the back of each mouse. Tumors were measured with a dial-caliper and the volumes were determined using the formula $width^2 \times length \times 0.52$. The treatment began 4 days after inoculation of the tumor cells. The therapeutic groups received TSP-1 or recombinant TSP-1 proteins IP daily, and the negative control group received comparable injections of saline alone. The experiments were terminated and mice sacrificed when the control mice began to die, usually at day 16 post-tumor cell injection.

Histological Examination.

The tumor tissues were cut, fixed with neutral buffered formaldehyde, and embedded in paraffin according to standard histological procedures. Hematoxylin and eosin staining was employed for tissue morphology examination. Blood vessels were immunochemically stained by anti-CD31 antibody with a Vectastain ABC kit (Vector Laboratories, Burlingame, Calif.). Tumor cell apoptosis was detected by TUNEL assay (Abe, M. et al., *Anal. Biochem*, 216:276–84, 1994). The number of blood vessels was recorded by counting ten high-power fields. Tumor cell proliferation and the apoptotic index were estimated by the percentage of cells scored under a light microscope. A minimum of 1,000 cells was counted in each tumor sample.

Inhibition of Experimental Tumor Growth by Recombinant Proteins

Figure 3A:
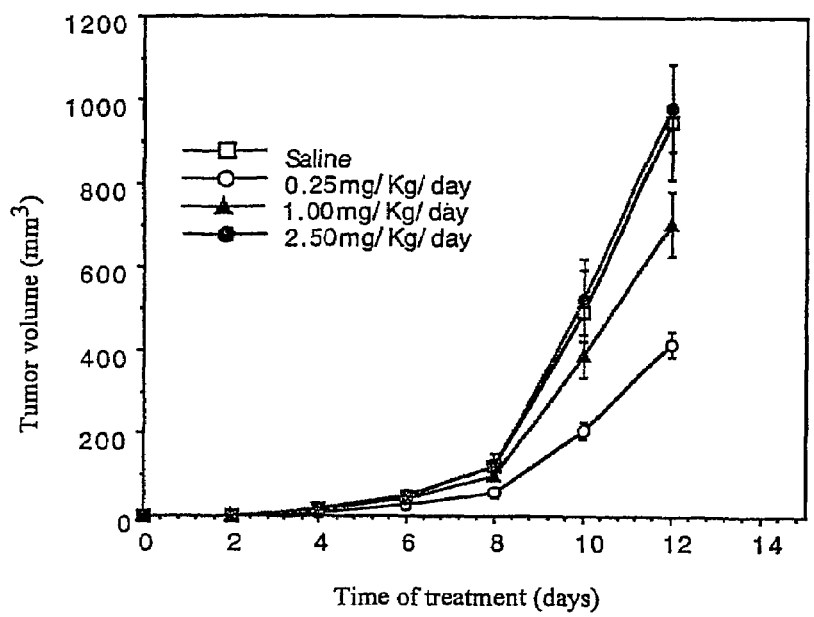
FIGS. 3A and 3B are graphs showing growth of B16F10 tumors in mice treated with platelet TSP-1 (FIG. 3A) or 3TSR protein (FIG. 3B). Each treatment group contained six mice. Treatment was initiated four days after subcutaneous injection of $1\times10^6$ tumor cells. The mice received one IP injection each day of saline (open squares), or 0.25 mg/kg/day (open circles), 1.0 mg/kg/day (filled triangles) or 2.5 mg/kg/day (filled circles) of 3TSR protein as described in the Examples. Tumor volume was determined every other day with a dial caliper. The mean and standard error are plotted.
Figure 3B:
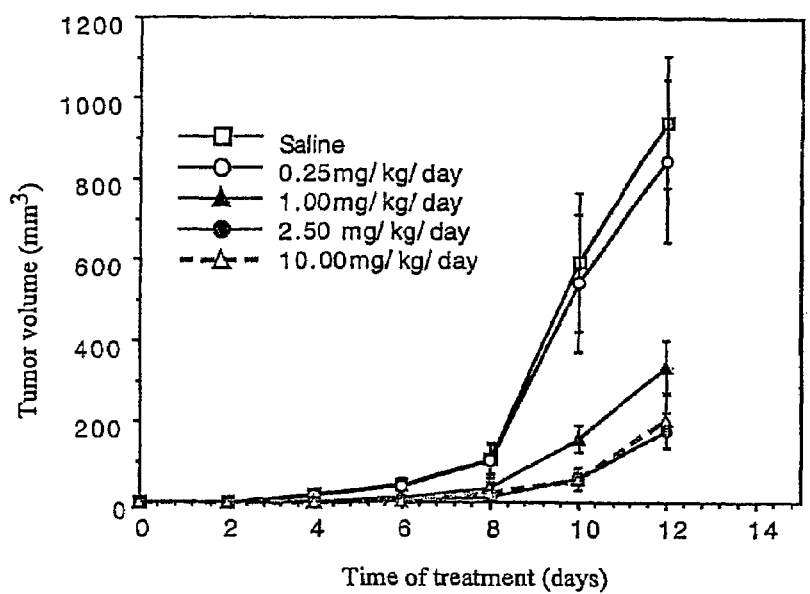

The B16F10 and the Lewis lung carcinoma models of experimental tumor growth have been used to assay the effect of the recombinant proteins. These models have been used extensively to assay the activity of the anti-angiogenic proteins endostatin, angiostatin and anti-thrombin III (O'Reilly, M. S. et al. *Science*, 285:1926–8, 1999; O'Reilly, M. S. et al, *Cell* 88:277–85, 1997; Boehm, T. et al., *Nature* 390:404–407, 1997). Systemic injection of TSP-1 (0.25 mg/ml) into tumor-bearing mice inhibits tumor growth (FIG. 3A) by 56% on the twelfth treatment day. At higher doses less inhibition is observed and a dose of 2.5 mg/kg/day has no effect on tumor growth. The 3TSR protein is a less effective inhibitor of tumor growth at 0.25 mg/kg/day than the intact protein (FIG. 3B). By contrast, at dosages of 1.0 mg/kg/day and greater, the 3TSR protein is more effective than TSP-1. Tumor volume is reduced by 81% by the 3TSR protein with a dose of 2.5 mg/kg/day and it remains maximally active at 10 mg/kg/day.

Figure 4:
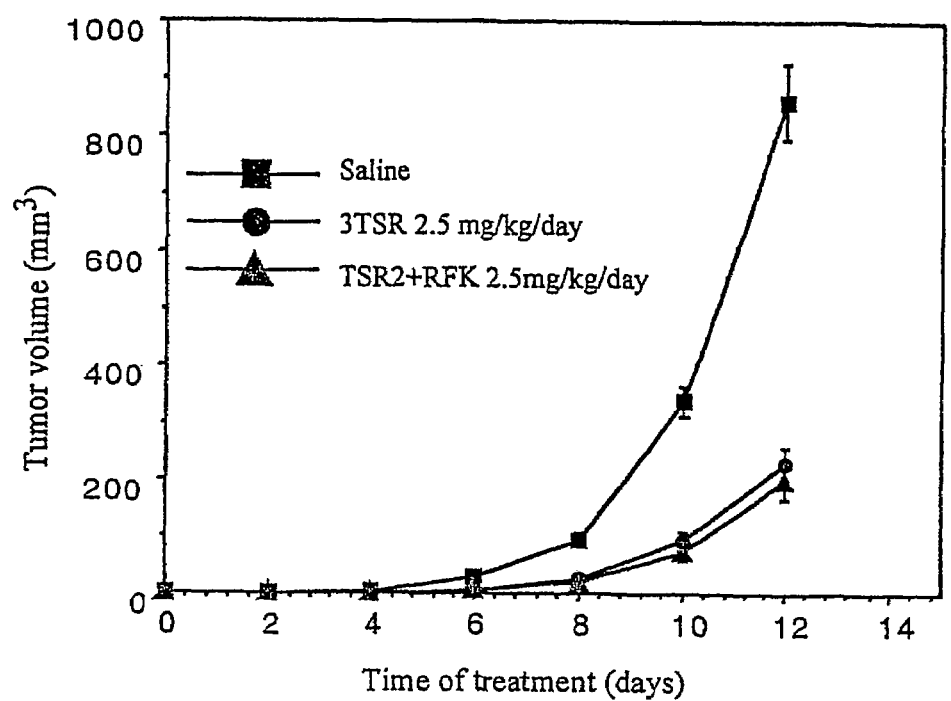
FIG. 4 is a graph showing growth of Lewis lung carcinoma in mice treated with recombinant proteins. Each treatment group contained six mice. Treatment was initiated four days after subcutaneous injections of $1\times10^6$ tumor cells. The mice received an IP injection each day of saline (filled squares), or the 3TSR protein (filled circles) or the TSR2+RFK protein (filled triangles). The recombinant proteins were used at a dose of 2.5 mg/kg/day. Tumor volume was determined every other day with dial caliper. The mean and standard error are plotted.
Figure 5A:
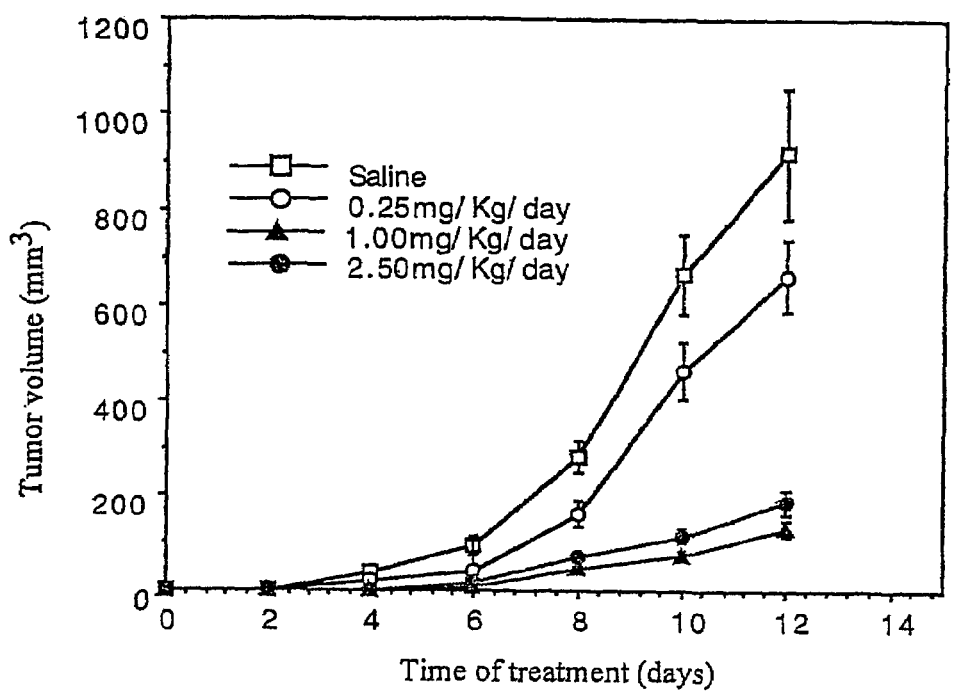
FIGS. 5A and 5B are graphs showing the growth of B16F10 tumors in mice treated with TSR2+RFK protein (FIG. 5A) or TSR2 protein (FIG. 5B). Each treatment group contained six mice. Treatment was initiated four days after subcutaneous injection of $1\times10^6$ tumor cells. The mice received one IP injection each day of saline (open squares), or 0.25 mg/kg/day (open circles), 1.0 mg/kg/day (filled triangles) or 2.5 mg/kg/day (filled circles) of recombinant protein. Tumor volume was determined every other day with a dial caliper. The mean and standard error are plotted.
Figure 5B:
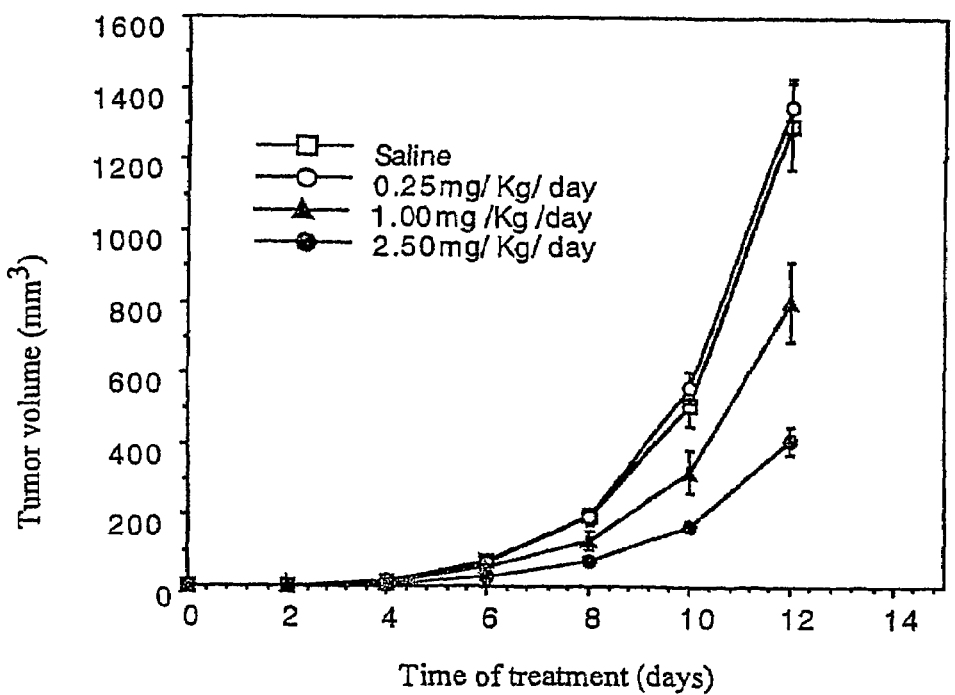

The inhibitory effect of the 3TSR protein is also observed in mice bearing experimental tumors that are formed by subcutaneous injection of Lewis lung carcinoma cells. At 2.5 mg/kg/day, the 3TSR protein inhibits tumor growth by 73% on treatment day 12 (FIG. 4). The TSR2+RFK protein is equally as effective as the 3TSR protein on a weight basis. For B16F10 and Lewis lung carcinoma cell-derived tumors, this protein inhibits tumor growth by 86% and 77%, respectively (FIGS. 4 and 5A).

Figures 6A, 6B, 6C:
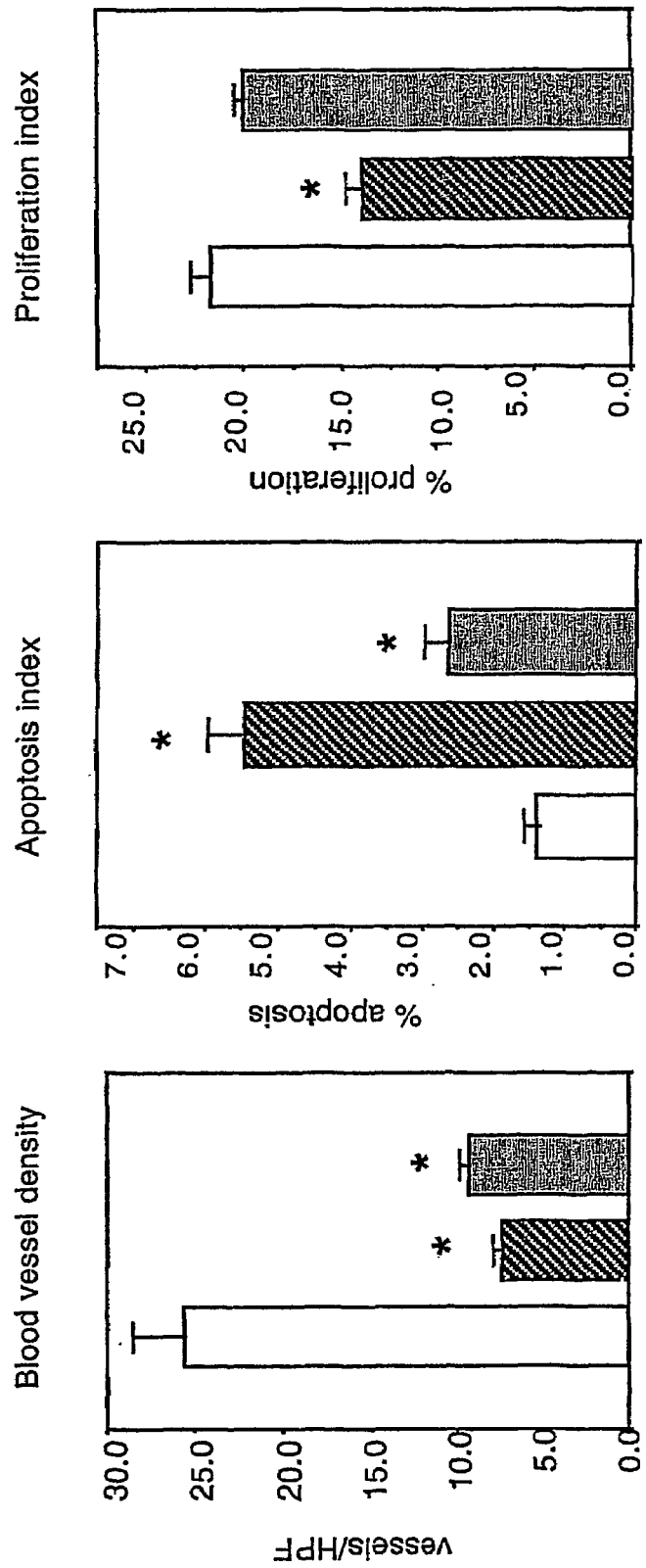
FIGS. 6A, 6B and 6C are bar graphs showing the quantitation of blood vessels (FIG. 6A), tumor cell apoptosis (FIG. 6B), and tumor cell proliferation (FIG. 6C). Tumors from mice treated with saline (solid bars), 1.0 mg/kg/day of TSR2+RFK protein (hatched bars) or 1.0 mg/kg/day of TSR2 protein (shaded bars) were fixed and tissue was prepared for histology. The asterisk indicates p<0.005 as compared to control in all cases except the level of apoptosis induced by TSR2 (FIG. 6B, shaded bar) where p≦0.025. A comparison of the vessel density for the mice treated with the TSR2+RFK (FIG. 6A, hatched bar) or TSR2 (FIG. 6A, shaded bar) yields p≦0.05.

To explore the potential involvement of the RFK sequence in the inhibition of B16F10 tumor growth, the TSR2+RFK, and TSR2 proteins, have been assayed. The tumor inhibition effect of the TSR2+RFK protein was comparable to that of the 3TSR protein at the various doses used (FIGS. 4B and 6A). By contrast, TSR2 is significantly less effective (FIG. 6B). At 0.25 mg/kg/day, the tumor growth in the mice treated with the TSR2 protein was indistinguishable from the control group. At 1.0 mg/kg/day, the TSR2+RFK protein inhibited tumor growth by 80%, while the TSR2 protein only inhibited growth by 38% on the twelfth day of treatment. At the highest dose tested (2.5 mg/kg/day), the difference was less pronounced with the TSR2+RFK and TSR2 proteins inhibiting tumor growth by 86% and 68%, respectively.

To better understand the effect of the recombinant protein treatment on tumor growth, we have determined the rate of proliferation, the apoptotic index and the capillary density for tumors in the saline control group, mice treated with the TSR2+RFK protein or mice treated with the TSR2 protein at an intermediate dose (1.0 mg/kg/day) where the largest effect of inclusion of the RFK sequence is observed. Tumors were removed and fixed on the twelfth treatment day. Capillaries were visualized with anti-CD31 antibody and apoptotic cells were identified by TUNEL. Tumors displayed a 71% and 64% reduction in capillary density when the mice were treated with the TSR2+RFK and TSR2 proteins, respectively (FIG. 6A). Whereas the tumors from mice that were treated with the TSR2+RFK protein displayed a 4-fold increase in tumor cell apoptosis p<0.005), the tumors from the mice that were treated with the TSR2 protein displayed only a 1.9-fold increase in apoptosis ($p \leq 0.025$) (FIG. 6B). The TSR2+RFK protein also reduced the percentage of PCNA positive tumor cells. The number of proliferating cells was decreased by 35% by treatment with the TSR2+RFK protein (p<0.005), while treatment with the TSR2 protein reduced tumor cell proliferation by 7.8% (p<0.05) (FIG. 6C).

Constructs for Expression of TSR2+QFK and 3TSR (TSP-2) Polypeptides

A recombinant protein in which arginine (413) was mutated to glutamine was prepared using the forward primer 605 htsp1f (GAT GAT CCC GGG GAC AAG CAA TTT AAA CAG GAT GG; SEQ ID NO: 17) and the reverse primer 515 htsp1r (GAT ACC GGT GAT GGG GCA GGC GTC TTT CTT; SEQ ID NO: 13). The resulting PCR product contains the glutamine codon CAA instead of the arginine codon AGA. The template for the PCR reaction was human thrombospondin-1 cDNA and the cloning sites were XmaI and AgeI in the pMT/BiP/V5-HisA vector. This approach is equivalent to that used for the construction of TSR2+RFK.

This approach was also used to construct the recombinant protein with all three TSRs of mouse TSP-2. In this case, a full-length cDNA clone for mouse TSP-2 was used as the template and the primers 544 mtsp2f (GAT GAT CCC GGG GAT GAG GGC TGG TCT CCG; SEQ ID NO: 18) and 545 mtsp2r (GAT ACC GGT AAT AGG GCA GCT TCT CTT; SEQ ID NO: 19) were used. The 3TSR (TSP-2) polypeptide of mouse consists of amino acids Asp 381 through Ile 550 (SEQ ID NO: 25) as shown in FIG. 10 (SEQ ID NO: 24). By similar methods, a 3TSR (TSP2) polypeptide of human could be made. See, for example, National Center for Biotechnology Information Accession No. NM 003247, *Homo sapiens* thrombospondin 2 mRNA. A polypeptide produced by these methods would consist of amino acids Glu 381 through Val 550.

Inhibition of B16F10 Experimental Tumor Growth by Various Recombinant Proteins TSR2, TSR2+RFK and TSR2+QFK.

Each treatment group contained six five- to eight-week old C57BL/6 mice. Treatment was initiated four days after subcutaneous injection of $1 \times 10^6$ B16F10 melanoma cells. The mice received one IP injection each day of saline, TSR2, TSR2+RFK or TSR2+QFK (SEQ ID NO: 23). A soluble form of the TGFβ receptor (100 μg/mouse/injection) (Smith, J. D. et al., *Circulation Research* 84:1212–1222, 1999) was included in the saline or TSR2+RFK injections on treatment day 1 and 7 for two additional experimental groups. The recombinant TSR-containing proteins were used at 1.0 mg/kg/day. Results are shown in FIG. 8.

Inhibition of B16F10 Experimental Tumor Growth by All Three Type 1 Repeats of Human TSP-1 or Mouse TSP-2.

Each treatment group contained six five- to eight-week old C57BL/6 mice. Treatment was initiated four days after subcutaneous injections of $1 \times 10^6$ B16F10 melanoma cells. The mice received one IP injection each day, of saline, all three type 1 repeats of human TSP-1 [3TSR (TSP1) in FIG. 9] or all three type 1 repeats of mouse TSP-2 [3TSR (TSP2) in FIG. 9]. Recombinant proteins were used at a dose of 2.5 mg/kg/day.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a polypeptide consisting of SEQ ID NO: 22, or a variant of the polypeptide, wherein the variant has at least about the same apoptotic or anti-angiogenic activity as the polypeptide, and wherein the variant is at least 70% identical to the polypeptide, and a pharmaceutically acceptable carrier.

2. A polypeptide consisting of amino acids 411–473 of human TSP-1 (SEQ ID NO: 22).

3. A method of inhibiting growth of angiogenesis dependent tumors in a patient, comprising administering to said patient an amount of the pharmaceutical composition of claim 1 sufficient to inhibit the growth of the tumors.

4. A method for inhibiting neovascularization in angiogenesis dependent tumors in a patient, said method comprising administering to the patient an amount of the pharmaceutical composition of claim 1 sufficient to inhibit neovascularization in said tumors.

5. A method of decreasing proliferation of angiogenesis dependent tumor cells in a patient, comprising administering to said patient an amount of the polypeptide of claim 2 sufficient to decrease proliferation of said tumor cells.

6. A method for inhibiting neovascularization in an angiogenesis dependent tumor or rumors in a patient, said method comprising administering to the patient an amount of the pharmaceutical composition of claim 2 sufficient to inhibit neovascularization in the tumor or tumors.

7. A polypeptide comprising the three type 1 repeats of human TSP-1 (SEQ ID NO: 20), but not comprising other domains of TSP-1.

8. A polypeptide comprising SEQ ID NO: 22, but not comprising other domains of TSP-1.

9. A polypeptide comprising all three type 1 repeats of human TSP-2 (SEQ ID NO: 27), but not other domains of TSP-2.

10. A pharmaceutical composition comprising a human 3TSR (TSP2) polypeptide (SEQ ID NO. 27), and a pharmaceutically acceptable carrier.

11. A method for reducing volume or inhibiting growth of an angiogenesis dependent tumor in a patient, comprising administering to the patient an amount of the polypeptide of claim 8 sufficient to reduce the volume of or inhibit the growth of said tumor.

12. A polypeptide consisting of SEQ ID NO: 20.

13. A method of inhibiting the growth of an angiogenesis dependent tumor in a patient, said method comprising administering to the patient an amount of the polypeptide of claim 12 sufficient to inhibit the growth of said tumor.

14. A method of inhibiting the growth of an angiogenesis dependent tumor in a patient, said method comprising administering to the patient an amount of the polypeptide of claim 7 sufficient to inhibit the growth of said tumor.

15. A method for inhibiting growth of melanoma tumors or lung tumors in a patient, said method comprising administering to the patient an amount of a polypeptide consisting of SEQ ID NO: 22 or a variant of the polypeptide, wherein the variant has at least about the same apoptotic or anti-angiogenic activity as the polypeptide, and wherein the variant is at least 70% identical to the polypeptide.

16. A method for inhibiting growth of melanoma tumors or lung tumors in a patient, said method comprising administering to the patient an amount of a polypeptide consisting of SEQ ID NO: 20 or a variant of the polypeptide, wherein the variant has at least about the same apoptotic or anti-angiogenic activity as the polypeptide, and wherein the variant is at least 70% identical to the polypeptide.

* * * * *

SEQUENCE LISTING

<160> NUMBER OF SEQ ID NOS: 27

<210> SEQ ID NO 1
<211> LENGTH: 1150
<212> TYPE: PRT
<213> ORGANISM: Homo sapiens

<400> SEQUENCE: 1

-continued

```
Asn Arg Ile Pro Glu Ser Gly Gly Asp Asn Ser Val Phe Asp Ile Phe
 1               5                  10                  15

Glu Leu Thr Gly Ala Ala Arg Lys Gly Ser Gly Arg Arg Leu Val Lys
                20                  25                  30

Gly Pro Asp Pro Ser Ser Pro Ala Phe Arg Ile Glu Asp Ala Asn Leu
            35                  40                  45

Ile Pro Pro Val Pro Asp Asp Lys Phe Gln Asp Leu Val Asp Ala Val
 50                  55                  60

Arg Thr Glu Lys Gly Phe Leu Leu Ala Ser Leu Arg Gln Met Lys
 65                  70                  75                  80

Lys Thr Arg Gly Thr Leu Leu Ala Leu Glu Arg Lys Asp His Ser Gly
                85                  90                  95

Gln Val Phe Ser Val Val Ser Asn Gly Lys Ala Gly Thr Leu Asp Leu
            100                 105                 110

Ser Leu Thr Val Gln Gly Lys Gln His Val Val Ser Val Glu Glu Ala
        115                 120                 125

Leu Leu Ala Thr Gly Gln Trp Lys Ser Ile Thr Leu Phe Val Gln Glu
130                 135                 140

Asp Arg Ala Gln Leu Tyr Ile Asp Cys Glu Lys Met Glu Asn Ala Glu
145                 150                 155                 160

Leu Asp Val Pro Ile Gln Ser Val Phe Thr Arg Asp Leu Ala Ser Ile
                165                 170                 175

Ala Arg Leu Arg Ile Ala Lys Gly Gly Val Asn Asp Asn Phe Gln Gly
            180                 185                 190

Val Leu Gln Asn Val Arg Phe Val Phe Gly Thr Thr Pro Glu Asp Ile
        195                 200                 205

Leu Arg Asn Lys Gly Cys Ser Ser Ser Thr Ser Val Leu Leu Thr Leu
        210                 215                 220

Asp Asn Asn Val Val Asn Gly Ser Ser Pro Ala Ile Arg Thr Asn Tyr
225                 230                 235                 240

Ile Gly His Lys Thr Lys Asp Leu Gln Ala Ile Cys Gly Ile Ser Cys
                245                 250                 255

Asp Glu Leu Ser Ser Met Val Leu Glu Leu Arg Gly Leu Arg Thr Ile
            260                 265                 270

Val Thr Thr Leu Gln Asp Ser Ile Arg Lys Val Thr Glu Glu Asn Lys
        275                 280                 285

Glu Leu Ala Asn Glu Leu Arg Arg Pro Pro Leu Cys Tyr His Asn Gly
        290                 295                 300

Val Gln Tyr Arg Asn Asn Glu Glu Trp Thr Val Asp Ser Cys Thr Glu
305                 310                 315                 320

Cys His Cys Gln Asn Ser Val Thr Ile Cys Lys Lys Val Ser Cys Pro
                325                 330                 335

Ile Met Pro Cys Ser Asn Ala Thr Val Pro Asp Gly Glu Cys Cys Pro
            340                 345                 350

Arg Cys Trp Pro Ser Asp Ser Ala Asp Asp Gly Trp Ser Pro Trp Ser
        355                 360                 365

Glu Trp Thr Ser Cys Ser Thr Ser Cys Gly Asn Cys Ile Gln Gln Arg
        370                 375                 380

Gly Arg Ser Cys Asp Ser Leu Asn Asn Arg Cys Glu Gly Ser Ser Val
385                 390                 395                 400

Gln Thr Arg Thr Cys His Ile Gln Glu Cys Asp Lys Arg Phe Lys Gln
                405                 410                 415
```

-continued

```
Asp Gly Gly Trp Ser His Trp Ser Pro Trp Ser Ser Cys Ser Val Thr
            420                 425                 430

Cys Gly Asp Gly Val Ile Thr Arg Ile Arg Leu Cys Asn Ser Pro Ser
        435                 440                 445

Pro Gln Met Asn Gly Lys Pro Cys Glu Gly Glu Ala Arg Glu Thr Lys
    450                 455                 460

Ala Cys Lys Lys Asp Ala Cys Pro Ile Asn Gly Gly Trp Gly Pro Trp
465                 470                 475                 480

Ser Pro Trp Asp Ile Cys Ser Val Thr Cys Gly Gly Gly Val Gln Lys
                485                 490                 495

Arg Ser Arg Leu Cys Asn Asn Pro Thr Pro Gln Phe Gly Gly Lys Asp
            500                 505                 510

Cys Val Gly Asp Val Thr Glu Asn Gln Ile Cys Asn Lys Gln Asp Cys
        515                 520                 525

Pro Ile Asp Gly Cys Leu Ser Asn Pro Cys Phe Ala Gly Val Lys Cys
    530                 535                 540

Thr Ser Tyr Pro Asp Gly Ser Trp Lys Cys Gly Ala Cys Pro Pro Gly
545                 550                 555                 560

Tyr Ser Gly His Gly Ile Gln Cys Thr Asp Val Asp Glu Cys Lys Glu
                565                 570                 575

Val Pro Asp Ala Cys Phe Asn His Asn Gly Glu His Arg Cys Glu Asn
            580                 585                 590

Thr Asp Pro Gly Tyr Asn Cys Leu Pro Cys Pro Pro Arg Phe Thr Gly
        595                 600                 605

Ser Gln Pro Phe Gly Gln Gly Val Glu His Ala Thr Ala Asn Lys Gln
    610                 615                 620

Val Cys Lys Pro Arg Asn Pro Cys Thr Asp Gly Thr His Asp Cys Asn
625                 630                 635                 640

Lys Asn Ala Lys Cys Asn Tyr Leu Gly His Tyr Ser Asp Pro Met Tyr
                645                 650                 655

Arg Cys Glu Cys Lys Pro Gly Tyr Ala Gly Asn Gly Ile Thr Cys Gly
            660                 665                 670

Glu Asp Thr Asp Leu Asp Gly Trp Pro Asn Glu Asn Leu Val Cys Val
        675                 680                 685

Ala Asn Ala Thr Tyr His Cys Lys Lys Asp Asn Cys Pro Asn Leu Pro
    690                 695                 700

Asn Ser Gly Gln Glu Asp Tyr Asp Lys Asp Gly Ile Gly Asp Ala Cys
705                 710                 715                 720

Asp Asp Asp Asp Asp Asn Asp Lys Ile Pro Asp Asp Arg Asp Asn Cys
                725                 730                 735

Pro Phe His Tyr Asn Pro Ala Gln Tyr Asp Tyr Asp Arg Asp Asp Val
            740                 745                 750

Gly Asp Arg Cys Asp Asn Cys Pro Tyr Asn His Asn Pro Asp Gln Ala
        755                 760                 765

Asp Thr Asp Asn Asn Gly Glu Gly Asp Ala Cys Ala Ala Asp Ile Asp
    770                 775                 780

Gly Asp Gly Ile Leu Asn Glu Arg Asp Asn Cys Gln Tyr Val Tyr Asn
785                 790                 795                 800

Val Asp Gln Arg Asp Thr Asp Met Asp Gly Val Gly Asp Gln Cys Asp
                805                 810                 815

Asn Cys Pro Leu Glu His Asn Pro Asp Gln Leu Asp Ser Asp Ser Asp
            820                 825                 830

Arg Ile Gly Asp Thr Cys Asp Asn Asn Gln Asp Ile Asp Glu Asp Gly
```

-continued

```
                835                 840                 845
His Gln Asn Asn Leu Asp Asn Cys Pro Tyr Val Pro Asn Ala Asn Gln
    850                 855                 860
Ala Asp His Asp Lys Asp Gly Lys Gly Asp Ala Cys Asp His Asp Asp
865                 870                 875                 880
Asp Asn Asp Gly Ile Pro Asp Lys Asp Asn Cys Arg Leu Val Pro
                885                 890                 895
Asn Pro Asp Gln Lys Asp Ser Asp Gly Asp Arg Gly Asp Ala Cys
            900                 905                 910
Lys Asp Asp Phe Asp His Asp Ser Val Pro Asp Ile Asp Ile Cys
        915                 920                 925
Pro Glu Asn Val Asp Ile Ser Glu Thr Asp Phe Arg Arg Phe Gln Met
    930                 935                 940
Ile Pro Leu Pro Lys Gly Thr Ser Gln Asn Asp Pro Asn Trp Val Val
945                 950                 955                 960
Arg His Gln Gly Lys Glu Leu Val Gln Thr Val Asn Cys Asp Pro Gly
                965                 970                 975
Leu Ala Val Gly Tyr Asp Glu Phe Asn Ala Val Asp Phe Ser Gly Thr
            980                 985                 990
Glu Phe Ile Asn Thr Glu Arg Asp Asp Asp Tyr Ala Gly Phe Val Phe
        995                 1000                1005
Gly Tyr Gln Ser Ser Ser Arg Phe Tyr Val Val Met Trp Lys Gln Val
    1010                1015                1020
Gln Ser Tyr Trp Asp Thr Asn Pro Thr Arg Ala Gln Gly Tyr Ser Gly
1025                1030                1035                1040
Leu Ser Val Lys Val Val Asn Ser Thr Gly Pro Gly Glu His Leu
                1045                1050                1055
Arg Asn Ala Leu Trp His Thr Gly Asn Thr Pro Gly Gln Val Arg Thr
            1060                1065                1070
Leu Trp His Asp Pro Arg His Ile Gly Trp Lys Asp Phe Thr Ala Tyr
        1075                1080                1085
Arg Trp Arg Leu Ser His Arg Pro Lys Thr Gly Phe Ile Arg Val Asn
    1090                1095                1100
Met Tyr Glu Gly Lys Lys Ile Met Ala Asp Ser Gly Pro Ile Tyr Asp
1105                1110                1115                1120
Lys Thr Tyr Ala Gly Gly Arg Leu Gly Leu Phe Val Phe Ser Gln Glu
                1125                1130                1135
Met Val Phe Phe Ser Asp Leu Lys Tyr Glu Cys Arg Asp Pro
            1140                1145                1150

<210> SEQ ID NO 2
<211> LENGTH: 5
<212> TYPE: PRT
<213> ORGANISM: Homo sapiens

<400> SEQUENCE: 2

Asp Lys Arg Phe Lys
 1               5

<210> SEQ ID NO 3
<211> LENGTH: 4
<212> TYPE: PRT
<213> ORGANISM: Homo sapiens

<400> SEQUENCE: 3

Lys Arg Phe Lys
```

```
1

<210> SEQ ID NO 4
<211> LENGTH: 7
<212> TYPE: PRT
<213> ORGANISM: Homo sapiens

<400> SEQUENCE: 4

Asn Gly Val Gln Tyr Arg Asn
1               5

<210> SEQ ID NO 5
<211> LENGTH: 6
<212> TYPE: PRT
<213> ORGANISM: Homo sapiens

<400> SEQUENCE: 5

Cys Ser Val Thr Cys Gly
1               5

<210> SEQ ID NO 6
<211> LENGTH: 7
<212> TYPE: PRT
<213> ORGANISM: Homo sapiens
<220> FEATURE:
<221> NAME/KEY: VARIANT
<222> LOCATION: 3, 6
<223> OTHER INFORMATION: Xaa = Any Amino Acid
<220> FEATURE:
<221> NAME/KEY: VARIANT
<222> LOCATION: 3, 6
<223> OTHER INFORMATION: Xaa = Any Amino Acid

<400> SEQUENCE: 6

Trp Ser Xaa Trp Ser Xaa Trp
1               5

<210> SEQ ID NO 7
<211> LENGTH: 6
<212> TYPE: PRT
<213> ORGANISM: Homo sapiens

<400> SEQUENCE: 7

Gly Gly Trp Ser His Trp
1               5

<210> SEQ ID NO 8
<211> LENGTH: 19
<212> TYPE: PRT
<213> ORGANISM: Homo sapiens

<400> SEQUENCE: 8

Ser Pro Trp Asp Ile Cys Ser Val Thr Cys Gly Gly Gly Val Gln Lys
1               5                   10                  15

Arg Ser Arg

<210> SEQ ID NO 9
<211> LENGTH: 33
<212> TYPE: PRT
<213> ORGANISM: Homo sapiens
<220> FEATURE:
<221> NAME/KEY: VARIANT
<222> LOCATION: 6, 7, 8, 9, 10, 11, 13, 14, 15, 16, 17, 18, 19, 20
<223> OTHER INFORMATION: Xaa = Any Amino Acid
<220> FEATURE:
<221> NAME/KEY: VARIANT
<222> LOCATION: 6, 7, 8, 9, 10, 11, 13, 14, 15, 16, 17, 18, 19, 20
```

<223> OTHER INFORMATION: Xaa = Any Amino Acid

<400> SEQUENCE: 9

Asp Val Asp Glu Cys Xaa Xaa Xaa Xaa Xaa Cys Xaa Xaa Xaa Xaa
1               5                   10                  15

Xaa Xaa Xaa Xaa Cys Glu Asn Thr Asp Pro Gly Tyr Asn Cys Leu Pro
            20              25                  30

Cys

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
gatgatcccg gggacgactc tgcggacgat ggc                           33

<210> SEQ ID NO 11
<211> LENGTH: 28
<212> TYPE: DNA
<213> ORGANISM: Artificial Sequence
<220> FEATURE:
<223> OTHER INFORMATION: PCR primer

<400> SEQUENCE: 11
gataccggta attggacagt cctgcttg                                 28

<210> SEQ ID NO 12
<211> LENGTH: 30
<212> TYPE: DNA
<213> ORGANISM: Artificial Sequence
<220> FEATURE:
<223> OTHER INFORMATION: PCR primer

<400> SEQUENCE: 12
gatgatcccg ggcaggatgg tggctggagc                               30

<210> SEQ ID NO 13
<211> LENGTH: 30
<212> TYPE: DNA
<213> ORGANISM: Artificial Sequence
<220> FEATURE:
<223> OTHER INFORMATION: PCR primer

<400> SEQUENCE: 13
gataccggtg atggggcagg cgtctttctt                               30

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14
gatgatcccg gggacaagag atttaaacag                               30

<210> SEQ ID NO 15
<211> LENGTH: 5
<212> TYPE: PRT
<213> ORGANISM: Artificial Sequence
<220> FEATURE:
<223> OTHER INFORMATION: vector-derived amino acid sequence -continued

```
<400> SEQUENCE: 15

Arg Ser Pro Trp Gly
1               5

<210> SEQ ID NO 16
<211> LENGTH: 8
<212> TYPE: PRT
<213> ORGANISM: Artificial Sequence
<220> FEATURE:
<223> OTHER INFORMATION: vector-derived amino acid sequence

<400> SEQUENCE: 16

Thr Gly His His His His His His
1               5

<210> SEQ ID NO 17
<211> LENGTH: 35
<212> TYPE: DNA
<213> ORGANISM: Artificial Sequence
<220> FEATURE:
<223> OTHER INFORMATION: PCR primer

<400> SEQUENCE: 17
gatgatcccg gggacaagca atttaaacag gatgg                              35

<210> SEQ ID NO 18
<211> LENGTH: 30
<212> TYPE: DNA
<213> ORGANISM: Artificial Sequence
<220> FEATURE:
<223> OTHER INFORMATION: PCR primer

<400> SEQUENCE: 18
gatgatcccg gggatgaggg ctggtctccg                                    30

<210> SEQ ID NO 19
<211> LENGTH: 27
<212> TYPE: DNA
<213> ORGANISM: Artificial Sequence
<220> FEATURE:
<223> OTHER INFORMATION: PCR primer

<400> SEQUENCE: 19
gataccggta atagggcagc ttctctt                                       27

<210> SEQ ID NO 20
<211> LENGTH: 170
<212> TYPE: PRT
<213> ORGANISM: Homo sapiens

<400> SEQUENCE: 20

Asp Asp Gly Trp Ser Pro Trp Ser Glu Trp Thr Ser Cys Ser Thr Ser
1               5                   10                  15

Cys Gly Asn Gly Ile Gln Gln Arg Gly Arg Ser Cys Asp Ser Leu Asn
                20                  25                  30

Asn Arg Cys Glu Gly Ser Ser Val Gln Thr Arg Thr Cys His Ile Gln
            35                  40                  45

Glu Cys Asp Lys Arg Phe Lys Gln Asp Gly Gly Trp Ser His Trp Ser
        50                  55                  60

Pro Trp Ser Ser Cys Ser Val Thr Cys Gly Asp Gly Val Ile Thr Arg
65                  70                  75                  80

Ile Arg Leu Cys Asn Ser Pro Ser Pro Gln Met Asn Gly Lys Pro Cys
```

```
                     85                  90                  95
Glu Gly Glu Ala Arg Glu Thr Lys Ala Cys Lys Lys Asp Ala Cys Pro
            100                 105                 110
Ile Asn Gly Gly Trp Gly Pro Trp Ser Pro Trp Asp Ile Cys Ser Val
            115                 120                 125
Thr Cys Gly Gly Val Gln Lys Arg Ser Arg Leu Cys Asn Asn Pro
            130                 135             140
Thr Pro Gln Phe Gly Gly Lys Asp Cys Val Gly Asp Val Thr Glu Asn
145                 150                 155                 160
Gln Ile Cys Asn Lys Gln Asp Cys Pro Ile
                165                 170

<210> SEQ ID NO 21
<211> LENGTH: 58
<212> TYPE: PRT
<213> ORGANISM: Homo sapiens

<400> SEQUENCE: 21

Gln Asp Gly Gly Trp Ser His Trp Ser Pro Trp Ser Ser Cys Ser Val
1               5                   10                  15
Thr Cys Gly Asp Gly Val Ile Thr Arg Ile Arg Leu Cys Asn Ser Pro
            20                  25                  30
Ser Pro Gln Met Asn Gly Lys Pro Cys Glu Gly Glu Ala Arg Glu Thr
        35                  40                  45
Lys Ala Cys Lys Lys Asp Ala Cys Pro Ile
    50                  55

<210> SEQ ID NO 22
<211> LENGTH: 63
<212> TYPE: PRT
<213> ORGANISM: Homo sapiens

<400> SEQUENCE: 22

Asp Lys Arg Phe Lys Gln Asp Gly Gly Trp Ser His Trp Ser Pro Trp
1               5                   10                  15
Ser Ser Cys Ser Val Thr Cys Gly Asp Gly Val Ile Thr Arg Ile Arg
            20                  25                  30
Leu Cys Asn Ser Pro Ser Pro Gln Met Asn Gly Lys Pro Cys Glu Gly
        35                  40                  45
Glu Ala Arg Glu Thr Lys Ala Cys Lys Lys Asp Ala Cys Pro Ile
    50                  55                  60

<210> SEQ ID NO 23
<211> LENGTH: 61
<212> TYPE: PRT
<213> ORGANISM: Artificial Sequence
<220> FEATURE:
<223> OTHER INFORMATION: engineered polypeptide

<400> SEQUENCE: 23

Gln Phe Lys Gln Asp Gly Gly Trp Ser His Trp Ser Pro Trp Ser Ser
1               5                   10                  15
Cys Ser Val Thr Cys Gly Asp Gly Val Ile Thr Arg Ile Arg Leu Cys
            20                  25                  30
Asn Ser Pro Ser Pro Gln Met Asn Gly Lys Pro Cys Glu Gly Glu Ala
        35                  40                  45
Arg Glu Thr Lys Ala Cys Lys Lys Asp Ala Cys Pro Ile
    50                  55                  60
```

```
<210> SEQ ID NO 24
<211> LENGTH: 1172
<212> TYPE: PRT
<213> ORGANISM: Mus musculus

<400> SEQUENCE: 24

Met Leu Trp Ala Leu Ala Leu Leu Ala Leu Gly Ile Gly Pro Arg Ala
 1               5                  10                  15

Ser Ala Gly Asp His Val Lys Asp Thr Ser Phe Asp Leu Phe Ser Ile
            20                  25                  30

Ser Asn Ile Asn Arg Lys Thr Ile Gly Ala Lys Gln Phe Arg Gly Pro
        35                  40                  45

Asp Pro Gly Val Pro Ala Tyr Arg Phe Val Arg Phe Asp Tyr Ile Pro
    50                  55                  60

Pro Val Asn Thr Asp Asp Leu Asn Arg Ile Val Lys Leu Ala Arg Arg
65                  70                  75                  80

Lys Glu Gly Phe Phe Leu Thr Ala Gln Leu Lys Gln Asp Arg Lys Ser
                85                  90                  95

Arg Gly Thr Leu Leu Val Leu Glu Gly Pro Gly Thr Ser Gln Arg Gln
            100                 105                 110

Phe Glu Ile Val Ser Asn Gly Pro Gly Asp Thr Leu Asp Leu Asn Tyr
        115                 120                 125

Trp Val Glu Gly Asn Gln His Thr Asn Phe Leu Glu Asp Val Gly Leu
    130                 135                 140

Ala Asp Ser Gln Trp Lys Asn Val Thr Val Gln Val Ala Ser Asp Thr
145                 150                 155                 160

Tyr Ser Leu Tyr Val Gly Cys Asp Leu Ile Asp Ser Val Thr Leu Glu
                165                 170                 175

Glu Pro Phe Tyr Glu Gln Leu Glu Val Asp Arg Ser Arg Met Tyr Val
            180                 185                 190

Ala Lys Gly Ala Ser Arg Glu Ser His Phe Arg Gly Leu Leu Gln Asn
        195                 200                 205

Val His Leu Val Phe Ala Asp Ser Val Glu Asp Ile Leu Ser Lys Lys
    210                 215                 220

Ser Cys Gln His Ser Gln Gly Ala Glu Val Asn Thr Ile Ser Glu His
225                 230                 235                 240

Thr Glu Thr Leu His Leu Ser Pro His Ile Thr Thr Asp Leu Val Val
                245                 250                 255

Gln Gly Val Glu Lys Ala Gln Glu Val Cys Thr His Ser Cys Glu Glu
            260                 265                 270

Leu Ser Asn Met Met Asn Glu Leu Ser Gly Leu His Val Met Val Asn
        275                 280                 285

Gln Leu Ser Lys Asn Leu Glu Arg Val Ser Ser Asp Asn Gln Phe Leu
    290                 295                 300

Leu Glu Leu Ile Gly Gly Pro Leu Lys Thr Arg Asn Met Ser Ala Cys
305                 310                 315                 320

Val Gln Glu Gly Arg Ile Phe Ala Glu Asn Glu Thr Trp Val Val Asp
                325                 330                 335

Ser Cys Thr Thr Cys Thr Cys Lys Lys Phe Lys Thr Val Cys His Gln
            340                 345                 350

Ile Thr Cys Ser Pro Ala Thr Cys Ala Asn Pro Ser Phe Val Glu Gly
        355                 360                 365

Glu Cys Cys Pro Ser Cys Ser His Ser Ala Asp Ser Asp Glu Gly Trp
    370                 375                 380
```

-continued

```
Ser Pro Trp Ala Glu Trp Thr Glu Cys Ser Val Thr Cys Gly Ser Gly
385                 390                 395                 400

Thr Gln Gln Arg Gly Arg Ser Cys Asp Val Thr Ser Asn Thr Cys Leu
            405                 410                 415

Gly Pro Ser Ile Gln Thr Arg Thr Cys Ser Leu Gly Lys Cys Asp Thr
                420                 425                 430

Arg Ile Arg Gln Asn Gly Gly Trp Ser His Trp Ser Pro Trp Ser Ser
        435                 440                 445

Cys Ser Val Thr Cys Gly Val Gly Asn Val Thr Arg Ile Arg Leu Cys
    450                 455                 460

Asn Ser Pro Val Pro Gln Met Gly Gly Lys Asn Cys Lys Gly Ser Gly
465                 470                 475                 480

Arg Glu Thr Lys Pro Cys Gln Arg Asp Pro Cys Pro Ile Asp Gly Arg
            485                 490                 495

Trp Ser Pro Trp Ser Pro Trp Ser Ala Cys Thr Val Thr Cys Ala Gly
                500                 505                 510

Gly Ile Arg Glu Arg Ser Arg Val Cys Asn Ser Pro Glu Pro Gln Tyr
        515                 520                 525

Gly Gly Lys Asp Cys Val Gly Asp Val Thr Glu His Gln Met Cys Asn
    530                 535                 540

Lys Arg Ser Cys Pro Ile Asp Gly Cys Leu Ser Asn Pro Cys Phe Pro
545                 550                 555                 560

Gly Ala Lys Cys Asn Ser Phe Pro Asp Gly Ser Trp Ser Cys Gly Ser
            565                 570                 575

Cys Pro Val Gly Phe Leu Gly Asn Gly Thr His Cys Glu Asp Leu Asp
                580                 585                 590

Glu Cys Ala Val Val Thr Asp Ile Cys Phe Ser Thr Asn Lys Ala Pro
        595                 600                 605

Arg Cys Val Asn Thr Asn Pro Gly Phe His Cys Leu Pro Cys Pro Pro
    610                 615                 620

Arg Tyr Lys Gly Asn Gln Pro Phe Gly Val Gly Leu Glu Asp Ala Arg
625                 630                 635                 640

Thr Glu Lys Gln Val Cys Glu Pro Glu Asn Pro Cys Lys Asp Lys Thr
            645                 650                 655

His Ser Cys His Lys Asn Ala Glu Cys Ile Tyr Leu Gly His Phe Ser
                660                 665                 670

Asp Pro Met Tyr Lys Cys Glu Cys Gln Ile Gly Tyr Ala Gly Asp Gly
        675                 680                 685

Leu Ile Cys Gly Glu Asp Ser Asp Leu Asp Gly Trp Pro Asn Asn Asn
    690                 695                 700

Leu Val Cys Ala Thr Asn Ala Thr Tyr His Cys Ile Lys Asp Asn Cys
705                 710                 715                 720

Pro Lys Leu Pro Asn Ser Gly Gln Glu Asp Phe Asp Lys Asp Gly Ile
            725                 730                 735

Gly Asp Ala Cys Asp Glu Asp Asp Asn Asp Gly Val Ser Asp Glu
                740                 745                 750

Lys Asp Asn Cys Gln Leu Leu Phe Asn Pro Arg Gln Leu Asp Tyr Asp
        755                 760                 765

Lys Asp Glu Val Gly Asp Arg Cys Asp Asn Cys Pro Tyr Val His Asn
    770                 775                 780

Pro Ala Gln Ile Asp Thr Asp Asn Asn Gly Glu Gly Asp Ala Cys Ser
785                 790                 795                 800
```

-continued

Val Asp Ile Asp Gly Asp Asp Val Phe Asn Glu Arg Asp Asn Cys Pro
            805                 810                 815

Tyr Val Tyr Asn Thr Asp Gln Arg Asp Thr Asp Gly Asp Gly Val Gly
            820                 825                 830

Asp His Cys Asp Asn Cys Pro Leu Met His Asn Pro Asp Gln Ile Asp
            835                 840                 845

Gln Asp Asn Asp Leu Val Gly Asp Gln Cys Asp Asn Asn Glu Asp Ile
        850                 855                 860

Asp Asp Asp Gly His Gln Asn Asn Gln Asp Asn Cys Pro Tyr Ile Ser
865                 870                 875                 880

Asn Ser Asn Gln Ala Asp His Asp Asn Asp Gly Lys Gly Asp Ala Cys
                885                 890                 895

Asp Ser Asp Asp Asp Asn Asp Gly Val Pro Asp Asp Arg Asp Asn Cys
                900                 905                 910

Arg Leu Val Phe Asn Pro Asp Gln Glu Asp Ser Asp Gly Asp Gly Arg
            915                 920                 925

Gly Asp Ile Cys Lys Asp Asp Phe Asp Asn Asp Asn Val Pro Asp Ile
        930                 935                 940

Asp Asp Val Cys Pro Glu Asn Asn Ala Ile Thr Glu Thr Asp Phe Arg
945                 950                 955                 960

Asn Phe Gln Met Val Pro Leu Asp Pro Lys Gly Thr Thr Gln Ile Asp
            965                 970                 975

Pro Asn Trp Val Ile Arg His Gln Gly Lys Glu Leu Val Gln Thr Ala
            980                 985                 990

Asn Ser Asp Pro Gly Ile Ala Val Gly Phe Asp Glu Phe Gly Ser Val
        995                 1000                1005

Asp Phe Ser Gly Thr Phe Tyr Val Asn Thr Asp Arg Asp Asp Asp Tyr
        1010                1015                1020

Ala Gly Phe Val Phe Gly Tyr Gln Ser Ser Ser Arg Phe Tyr Val Val
1025                1030                1035                1040

Met Trp Lys Gln Val Thr Gln Thr Tyr Trp Glu Asp Lys Pro Ser Arg
            1045                1050                1055

Ala Tyr Gly Tyr Ser Gly Val Ser Leu Lys Val Val Asn Ser Thr Thr
            1060                1065                1070

Gly Thr Gly Glu His Leu Arg Asn Ala Leu Trp His Thr Gly Asn Thr
        1075                1080                1085

Glu Gly Gln Val Arg Thr Leu Trp His Asp Pro Lys Asn Ile Gly Trp
1090                1095                1100

Lys Asp Tyr Thr Ala Tyr Arg Trp His Leu Ile His Arg Pro Lys Thr
1105                1110                1115                1120

Gly Tyr Met Arg Val Leu Val His Glu Gly Lys Gln Val Met Ala Asp
                1125                1130                1135

Ser Gly Pro Ile Tyr Asp Gln Thr Tyr Ala Gly Gly Arg Leu Gly Leu
            1140                1145                1150

Phe Val Phe Ser Gln Glu Met Val Tyr Phe Ser Asp Leu Lys Tyr Glu
        1155                1160                1165

Cys Arg Asp Ala
    1170

<210> SEQ ID NO 25
<211> LENGTH: 170
<212> TYPE: PRT
<213> ORGANISM: Mus musculus

<400> SEQUENCE: 25

```
Asp Glu Gly Trp Ser Pro Trp Ala Glu Trp Thr Glu Cys Ser Val Thr
1               5                   10                  15

Cys Gly Ser Gly Thr Gln Gln Arg Gly Arg Ser Cys Asp Val Thr Ser
            20                  25                  30

Asn Thr Cys Leu Gly Pro Ser Ile Gln Thr Arg Thr Cys Ser Leu Gly
        35                  40                  45

Lys Cys Asp Thr Arg Ile Arg Gln Asn Gly Gly Trp Ser His Trp Ser
50                      55                  60

Pro Trp Ser Ser Cys Ser Val Thr Cys Gly Val Gly Asn Val Thr Arg
65                  70                  75                  80

Ile Arg Leu Cys Asn Ser Pro Val Pro Gln Met Gly Gly Lys Asn Cys
                85                  90                  95

Lys Gly Ser Gly Arg Glu Thr Lys Pro Cys Gln Arg Asp Pro Cys Pro
            100                 105                 110

Ile Asp Gly Arg Trp Ser Pro Trp Ser Pro Trp Ser Ala Cys Thr Val
            115                 120                 125

Thr Cys Ala Gly Gly Ile Arg Glu Arg Ser Arg Val Cys Asn Ser Pro
        130                 135                 140

Glu Pro Gln Tyr Gly Gly Lys Asp Cys Val Gly Asp Val Thr Glu His
145                 150                 155                 160

Gln Met Cys Asn Lys Arg Ser Cys Pro Ile
                165                 170

<210> SEQ ID NO 26
<211> LENGTH: 1172
<212> TYPE: PRT
<213> ORGANISM: Homo sapiens

<400> SEQUENCE: 26

Met Val Trp Arg Leu Val Leu Leu Ala Leu Trp Val Trp Pro Ser Thr
1               5                   10                  15

Gln Ala Gly His Gln Asp Lys Asp Thr Thr Phe Asp Leu Phe Ser Ile
            20                  25                  30

Ser Asn Ile Asn Arg Lys Thr Ile Gly Ala Lys Gln Phe Arg Gly Pro
        35                  40                  45

Asp Pro Gly Val Pro Ala Tyr Arg Phe Val Arg Phe Asp Tyr Ile Pro
50                      55                  60

Pro Val Asn Ala Asp Asp Leu Ser Lys Ile Thr Lys Ile Met Arg Gln
65                  70                  75                  80

Lys Glu Gly Phe Phe Leu Thr Ala Gln Leu Lys Gln Asp Gly Lys Ser
                85                  90                  95

Arg Gly Thr Leu Leu Ala Leu Glu Gly Pro Gly Leu Ser Gln Arg Gln
            100                 105                 110

Phe Glu Ile Val Ser Asn Gly Pro Ala Asp Thr Leu Asp Leu Thr Tyr
            115                 120                 125

Trp Ile Asp Gly Thr Arg His Val Val Ser Leu Glu Asp Val Gly Leu
        130                 135                 140

Ala Asp Ser Gln Trp Lys Asn Val Thr Val Gln Val Ala Gly Glu Thr
145                 150                 155                 160

Tyr Ser Leu His Val Gly Cys Asp Leu Ile Gly Pro Val Ala Leu Asp
                165                 170                 175

Glu Pro Phe Tyr Glu His Leu Gln Ala Glu Lys Ser Arg Met Tyr Val
            180                 185                 190

Ala Lys Gly Ser Ala Arg Glu Ser His Phe Arg Gly Leu Leu Gln Asn
```

-continued

```
            195                 200                 205
Val His Leu Val Phe Glu Asn Ser Val Glu Asp Ile Leu Ser Lys Lys
    210                 215                 220

Gly Cys Gln Gly Gln Gly Ala Glu Ile Asn Ala Ile Ser Glu Asn
225                 230                 235                 240

Thr Glu Thr Leu Arg Leu Gly Pro His Val Thr Thr Glu Tyr Val Gly
                245                 250                 255

Pro Ser Ser Glu Arg Arg Pro Glu Val Cys Glu Arg Ser Cys Glu Glu
                260                 265                 270

Leu Gly Asn Met Val Gln Glu Leu Ser Gly Leu His Val Leu Val Asn
                275                 280                 285

Gln Leu Ser Glu Asn Leu Lys Arg Val Ser Asn Asp Asn Gln Phe Leu
        290                 295                 300

Trp Glu Leu Ile Gly Gly Pro Pro Lys Thr Arg Asn Met Ser Ala Cys
305                 310                 315                 320

Trp Gln Asp Gly Arg Phe Phe Ala Glu Asn Glu Thr Trp Val Val Asp
                325                 330                 335

Ser Cys Thr Thr Cys Thr Cys Lys Lys Phe Lys Thr Ile Cys His Gln
                340                 345                 350

Ile Thr Cys Pro Pro Ala Thr Cys Ala Ser Pro Ser Phe Val Glu Gly
                355                 360                 365

Glu Cys Cys Pro Ser Cys Leu His Ser Val Asp Gly Glu Glu Gly Trp
370                 375                 380

Ser Pro Trp Ala Glu Trp Thr Gln Cys Ser Val Thr Cys Gly Ser Gly
385                 390                 395                 400

Thr Gln Gln Arg Gly Arg Ser Cys Asp Val Thr Ser Asn Thr Cys Leu
                405                 410                 415

Gly Pro Ser Ile Gln Thr Arg Ala Cys Ser Leu Ser Lys Cys Asp Thr
                420                 425                 430

Arg Ile Arg Gln Asp Gly Gly Trp Ser His Trp Ser Pro Trp Ser Ser
        435                 440                 445

Cys Ser Val Thr Cys Gly Val Gly Asn Ile Thr Arg Ile Arg Leu Cys
450                 455                 460

Asn Ser Pro Val Pro Gln Met Gly Gly Lys Asn Cys Lys Gly Ser Gly
465                 470                 475                 480

Arg Glu Thr Lys Ala Cys Gln Gly Ala Pro Cys Pro Ile Asp Gly Arg
                485                 490                 495

Trp Ser Pro Trp Ser Pro Trp Ser Ala Cys Thr Val Thr Cys Ala Gly
                500                 505                 510

Gly Ile Arg Glu Arg Thr Arg Val Cys Asn Ser Pro Glu Pro Gln Tyr
        515                 520                 525

Gly Gly Lys Ala Cys Val Gly Asp Val Gln Glu Arg Gln Met Cys Asn
        530                 535                 540

Lys Arg Ser Cys Pro Val Asp Gly Cys Leu Ser Asn Pro Cys Phe Pro
545                 550                 555                 560

Gly Ala Gln Cys Ser Ser Phe Pro Asp Gly Ser Trp Ser Cys Gly Phe
                565                 570                 575

Cys Pro Val Gly Phe Leu Gly Asn Gly Thr His Cys Glu Asp Leu Asp
                580                 585                 590

Glu Cys Ala Leu Val Pro Asp Ile Cys Phe Ser Thr Ser Lys Val Pro
        595                 600                 605

Arg Cys Val Asn Thr Gln Pro Gly Phe His Cys Leu Pro Cys Pro Pro
610                 615                 620
```

-continued

```
Arg Tyr Arg Gly Asn Gln Pro Val Gly Val Gly Leu Glu Ala Ala Lys
625                 630                 635                 640

Thr Glu Lys Gln Val Cys Glu Pro Glu Asn Pro Cys Lys Asp Lys Thr
                645                 650                 655

His Asn Cys His Lys His Ala Glu Cys Ile Tyr Leu Gly His Phe Ser
            660                 665                 670

Asp Pro Met Tyr Lys Cys Glu Cys Gln Thr Gly Tyr Ala Gly Asp Gly
        675                 680                 685

Leu Ile Cys Gly Glu Asp Ser Asp Leu Asp Gly Trp Pro Asn Leu Asn
    690                 695                 700

Leu Val Cys Ala Thr Asn Ala Thr Tyr His Cys Ile Lys Asp Asn Cys
705                 710                 715                 720

Pro His Leu Pro Asn Ser Gly Gln Glu Asp Phe Asp Lys Asp Gly Ile
                725                 730                 735

Gly Asp Ala Cys Asp Asp Asp Asp Asn Asp Gly Val Thr Asp Glu
            740                 745                 750

Lys Asp Asn Cys Gln Leu Leu Phe Asn Pro Arg Gln Ala Asp Tyr Asp
755                 760                 765

Lys Asp Glu Val Gly Asp Arg Cys Asp Asn Cys Pro Tyr Val His Asn
770                 775                 780

Pro Ala Gln Ile Asp Thr Asp Asn Asn Gly Glu Gly Asp Ala Cys Ser
785                 790                 795                 800

Val Asp Ile Asp Gly Asp Asp Val Phe Asn Glu Arg Asp Asn Cys Pro
            805                 810                 815

Tyr Val Tyr Asn Thr Asp Gln Arg Asp Thr Asp Gly Asp Gly Val Gly
        820                 825                 830

Asp His Cys Asp Asn Cys Pro Leu Val His Asn Pro Asp Gln Thr Asp
    835                 840                 845

Val Asp Asn Asp Leu Val Gly Asp Gln Cys Asp Asn Asn Glu Asp Ile
850                 855                 860

Asp Asp Asp Gly His Gln Asn Asn Gln Asp Asn Cys Pro Tyr Ile Ser
865                 870                 875                 880

Asn Ala Asn Gln Ala Asp His Asp Arg Asp Gly Gln Gly Asp Ala Cys
                885                 890                 895

Asp Pro Asp Asp Asp Asn Asp Gly Val Pro Asp Arg Asp Asn Cys
            900                 905                 910

Arg Leu Val Phe Asn Pro Asp Gln Glu Asp Leu Asp Gly Asp Gly Arg
        915                 920                 925

Gly Asp Ile Cys Lys Asp Asp Phe Asp Asn Asp Asn Ile Pro Asp Ile
    930                 935                 940

Asp Asp Val Cys Pro Glu Asn Asn Ala Ile Ser Glu Thr Asp Phe Arg
945                 950                 955                 960

Asn Phe Gln Met Val Pro Leu Asp Pro Lys Gly Thr Thr Gln Ile Asp
                965                 970                 975

Pro Asn Trp Val Ile Arg His Gln Gly Lys Glu Leu Val Gln Thr Ala
            980                 985                 990

Asn Ser Asp Pro Gly Ile Ala Val Gly Phe Asp Glu Phe Gly Ser Val
        995                 1000                1005

Asp Phe Ser Gly Thr Phe Tyr Val Asn Thr Asp Arg Asp Asp Asp Tyr
    1010                1015                1020

Ala Gly Phe Val Phe Gly Tyr Gln Ser Ser Ser Arg Phe Tyr Val Val
1025                1030                1035                1040
```

```
Met Trp Lys Gln Val Thr Gln Thr Tyr Trp Glu Asp Gln Pro Thr Arg
                1045                1050                1055

Ala Tyr Gly Tyr Ser Gly Val Ser Leu Lys Val Val Asn Ser Thr Thr
            1060                1065                1070

Gly Thr Gly Glu His Leu Arg Asn Ala Leu Trp His Thr Gly Asn Thr
        1075                1080                1085

Pro Gly Gln Val Arg Thr Leu Trp His Asp Pro Arg Asn Ile Gly Trp
    1090                1095                1100

Lys Asp Tyr Thr Ala Tyr Arg Trp His Leu Thr His Arg Pro Lys Thr
1105                1110                1115                1120

Gly Tyr Ile Arg Val Leu Val His Glu Gly Lys Gln Val Met Ala Asp
                1125                1130                1135

Ser Gly Pro Ile Tyr Asp Gln Thr Tyr Ala Gly Gly Arg Leu Gly Leu
            1140                1145                1150

Phe Val Phe Ser Gln Glu Met Val Tyr Phe Ser Asp Leu Lys Tyr Glu
        1155                1160                1165

Cys Arg Asp Ile
    1170

<210> SEQ ID NO 27
<211> LENGTH: 170
<212> TYPE: PRT
<213> ORGANISM: Homo sapiens

<400> SEQUENCE: 27

Glu Glu Gly Trp Ser Pro Trp Ala Glu Trp Thr Gln Cys Ser Val Thr
1               5                   10                  15

Cys Gly Ser Gly Thr Gln Gln Arg Gly Arg Ser Cys Asp Val Thr Ser
            20                  25                  30

Asn Thr Cys Leu Gly Pro Ser Ile Gln Thr Arg Ala Cys Ser Leu Ser
        35                  40                  45

Lys Cys Asp Thr Arg Ile Arg Gln Asp Gly Gly Trp Ser His Trp Ser
50                  55                  60

Pro Trp Ser Ser Cys Ser Val Thr Cys Gly Val Gly Asn Ile Thr Arg
65                  70                  75                  80

Ile Arg Leu Cys Asn Ser Pro Val Pro Gln Met Gly Gly Lys Asn Cys
                85                  90                  95

Lys Gly Ser Gly Arg Glu Thr Lys Ala Cys Gln Gly Ala Pro Cys Pro
            100                 105                 110

Ile Asp Gly Arg Trp Ser Pro Trp Ser Pro Trp Ser Ala Cys Thr Val
        115                 120                 125

Thr Cys Ala Gly Gly Ile Arg Glu Arg Thr Arg Val Cys Asn Ser Pro
    130                 135                 140

Glu Pro Gln Tyr Gly Gly Lys Ala Cys Val Gly Asp Val Gln Glu Arg
145                 150                 155                 160

Gln Met Cys Asn Lys Arg Ser Cys Pro Val
                165                 170
```